US005484584A

United States Patent [19]
Wallace et al.

[11] Patent Number: 5,484,584
[45] Date of Patent: Jan. 16, 1996

[54] THERAPEUTIC AND DIAGNOSTIC USE OF MODIFIED POLYMERIC MICROCAPSULES

[75] Inventors: Sidney Wallace, Houston; David Yang, Sugar Lan; Michael Wallace, Houston; Chun Li, Houston; Li-Ren Kuang, Houston, all of Tex.

[73] Assignee: Board of Regents, The University of Texas System, Austin, Tex.

[21] Appl. No.: 916,348

[22] Filed: Jul. 17, 1992

Related U.S. Application Data

[63] Continuation-in-part of Ser. No. 592,020, Oct. 2, 1990, abandoned.

[51] Int. Cl.⁶ ............................ A61K 51/00; B01J 13/02; B32B 5/16
[52] U.S. Cl. ..................... 424/129; 424/497; 424/499; 424/491; 424/501; 424/9.45; 424/9.4; 428/402.21; 427/212.31; 264/4.3; 264/4.33
[58] Field of Search ..................... 424/497, 499, 424/501, 491, 9, 1.29; 428/402.21; 427/213.31; 264/4.3, 4.33

[56] References Cited

U.S. PATENT DOCUMENTS

| | | | |
|---|---|---|---|
| 3,891,570 | 6/1975 | Fukushima et al. | 252/31633 14 |
| 4,138,383 | 2/1979 | Rembaum et al. | 525/54.1 X |
| 4,230,685 | 10/1980 | Senyai et al. | 436/526 |
| 4,267,234 | 5/1981 | Rembaum et al. | 424/497 X |
| 4,272,398 | 6/1981 | Jaffe | 252/316 |
| 4,413,070 | 11/1983 | Rembaum | 424/491 X |
| 4,479,911 | 10/1984 | Fong | 264/4.6 |
| 4,492,720 | 1/1985 | Mosier | 427/213.3 |
| 4,552,812 | 11/1985 | Margel et al. | 428/402.24 X |
| 4,671,954 | 6/1987 | Goldberg et al. | 424/491 X |
| 4,871,716 | 10/1989 | Longo et al. | 424/491 X |
| 4,931,362 | 6/1990 | Zsifkovits et al. | 428/402.22 |
| 4,933,105 | 6/1990 | Fong | 252/303 |
| 4,994,281 | 2/1991 | Muranishi et al. | 424/497 |
| 5,059,542 | 10/1991 | Hirai et al. | 525/54.1 X |
| 5,069,936 | 12/1991 | Yen | 424/491 X |
| 5,100,669 | 3/1992 | Hyon et al. | 424/426 |
| 5,194,300 | 3/1993 | Cheung | 525/54.1 X |
| 5,238,714 | 8/1993 | Wallace et al. | 434/497 X |

FOREIGN PATENT DOCUMENTS

| | | |
|---|---|---|
| 0302582 | 8/1989 | European Pat. Off. |
| 0326722 | 9/1989 | European Pat. Off. ........ A01N 25/28 |
| 0350246 | 10/1990 | European Pat. Off. ......... A61K 9/52 |

OTHER PUBLICATIONS

Sidman et al., *Biopolymers*, vol. 22, No. 1, pp. 547–556 (Jan. 1983).

Kuroyanagi et al., *J. Poly. Sci. Poly. Chem. Ed.*, vol. 21, No. 5, pp. 1289–1303 (May 1983).

(List continued on next page.)

*Primary Examiner*—Gary L. Geist
*Assistant Examiner*—C. Harris
*Attorney, Agent, or Firm*—Arnold, White & Durkee

[57] ABSTRACT

The present invention relates to a highly efficient method of preparing modified microcapsules exhibiting selective targeting. These microcapsules are suitable for encapsulation surface attachment of therapeutic and diagnostic agents. In one aspect of the invention, surface charge of the polymeric material is altered by conjugation of an amino acid ester to the providing improved targeting of encapsulated agents to specific tissue cells. Examples include encapsulation of radiodiagnostic agents in 1 μm capsules to provide improved opacification and encapsulation of cytotoxic agents in 100 μm capsules for chemoembolization procedures. The microcapsules are suitable for attachment of a wide range of targeting agents, including antibodies, steroids and drugs, which may be attached to the microcapsule polymer before or after formation of suitably sized microcapsules. The invention also includes microcapsules surface modified with hydroxyl groups. Various agents such as estrone may be attached to the microcapsules and effectively targeted to selected organs.

14 Claims, 35 Drawing Sheets

OTHER PUBLICATIONS

Asano et al., *Makramol. Chem.*, vol. 184, No. 9, pp. 1761–1770 9Sep. 1983).

Nishimura et al., *Makromol. Chem.*, vol. 185, No. 10, pp. 2109–2116 (Oct. 1984).

International Search Report, mailed Jan. 7, 1994.

Article by Wright et al., "Microcapsules for arterial chemoembolization: appearance and *in vitro* drug release characteristics", J. Microencapsulation, vol. 5, No. 1, pp. 13–20, 1988.

Article by Wright et al., "Regional Isolation–Perfusion: An Experimental Percutaneous Approach Tested and Compared with Arterial Occlusion–Infusion", Cardiovasc. Intervent. Radiol., vol. 7, pp. 294–298.

Article by Bechtel et al., "An Experimental Evaluation of Microcapsules for Arterial Chemoembolization", Radiology, vol. 161, pp. 601–604, 1986.

Article by Kawashima et al., "Drug Release Proeprties of the Microcapsules of Adriamycin Hydrochloride With Ethylcellulose Prepared by as Phase Separation Technique", Drug Development and Industrial Pharmacy, vol. 10, No. 3, pp. 467–479, 1984.

Article by Benita et al., "Characterizatin of Drug–Loaded Poly(d,l–lactide) Microspheres", J. of Pharm. Sci., vol. 73, No. 12, pp. 1721–1724, Dec. 1984.

Article by Tice and Gilley, "Preparation of Injectable Controlled–Release Microcapusles by a Solvent–Evaporation Process", J. of Controlled Release, vol. 2, pp. 343–352, 1985.

Article by Smith and Hunneyball, "Evaluation of poly(lactic acid) as a biodegradable drug delivery system for parenteral administration", Intl. J. of Pharm., vol. 30, pp. 215–200, 1986.

Sections 1.4–1.6, 3.1 and 3.4 of Book by Bruning and Kintz.

Dialog Search –Abstracts of reference relating to microencapsulation and sustained drug delivery.

Dialog Search —Abstracts of references relating to microencapsulation of therapeutic agents.

Jalil and Nixon, "Biodegradable Poly(lactic acid) and Poly(lactide–Co–Glycolide) Microcapsules: Problems Associated with Preparative Techniques and Release Properties," J. Microencapsulation, 7(3):297–325, 1990.

PCT Search Report mailed Apr. 27, 1992.

Chemical Abstracts 114:253937b (Jul. 1, 1991) Cho et al.

Tabata et al., *J. Biomed. Mater Res.*, vol. 22, No. 9 (1988) "Macropohage phagocytosis of biodegradable microspheres composed of L–lactic acid/glycolic acid homo–and co–polymers", pp. 837–858.

Yokoyama et al., *J. Biomed. Mater. Res.*, vol. 20, No. 7 (1986) "Adhesion behavior of rat lymphocytes to poly(ether)–poly (amino acid) block and graft coploymers", pp. 687–678.

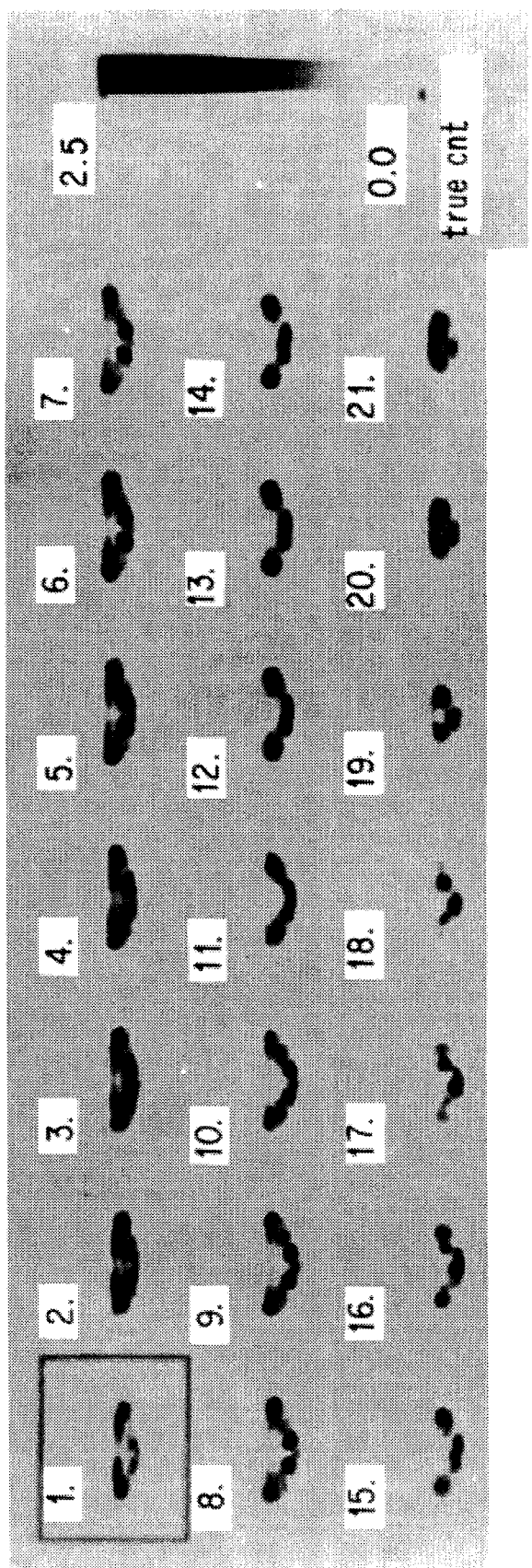
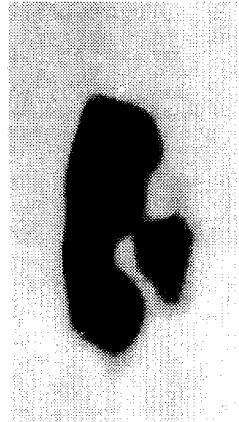
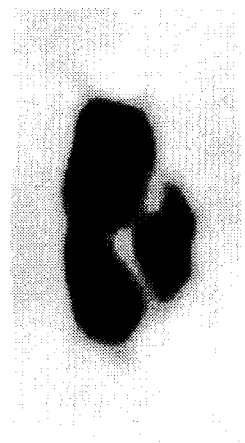
FIG. 20D

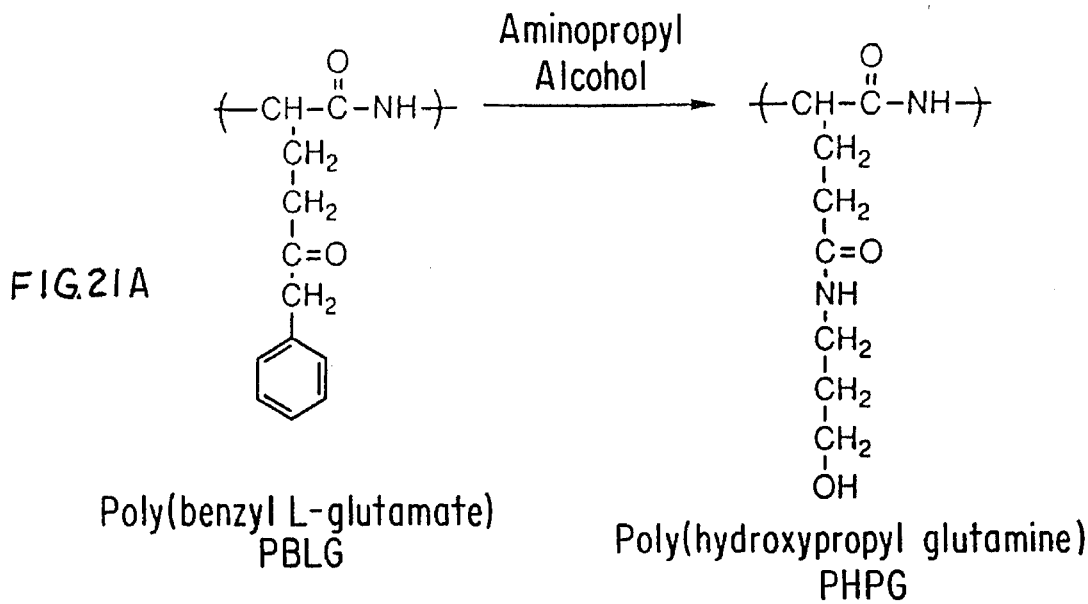
FIG. 21A
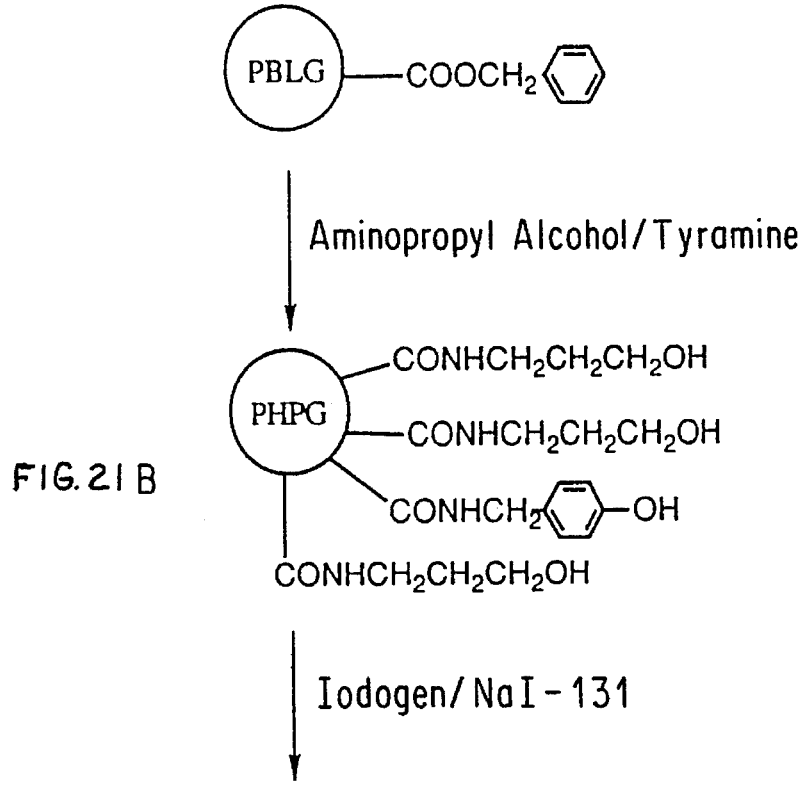
FIG. 21B
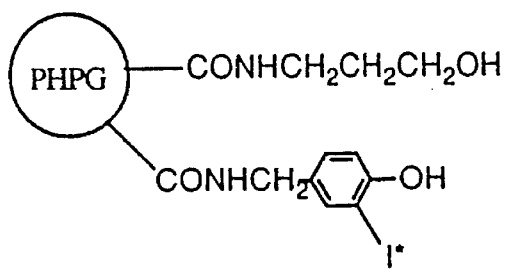

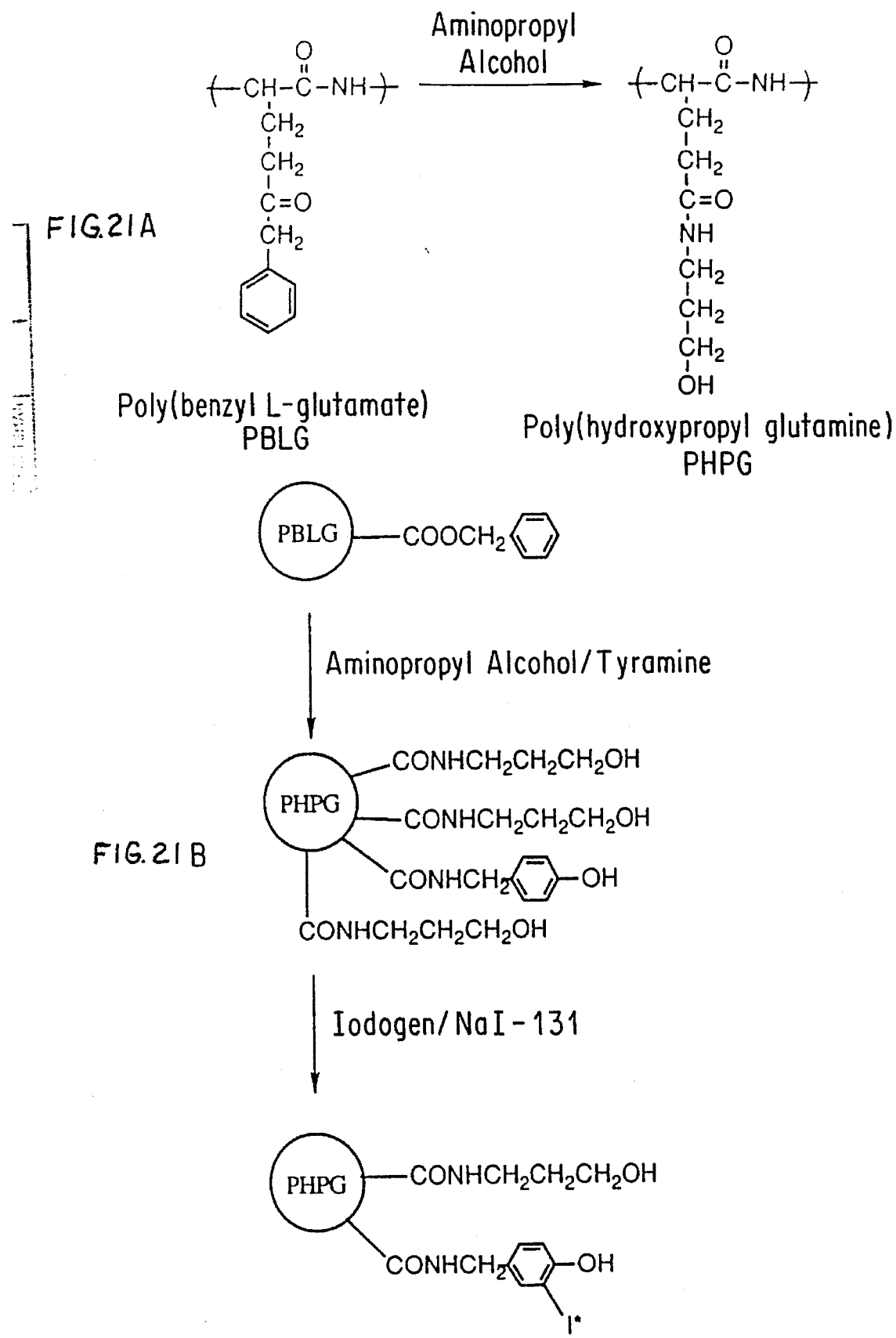

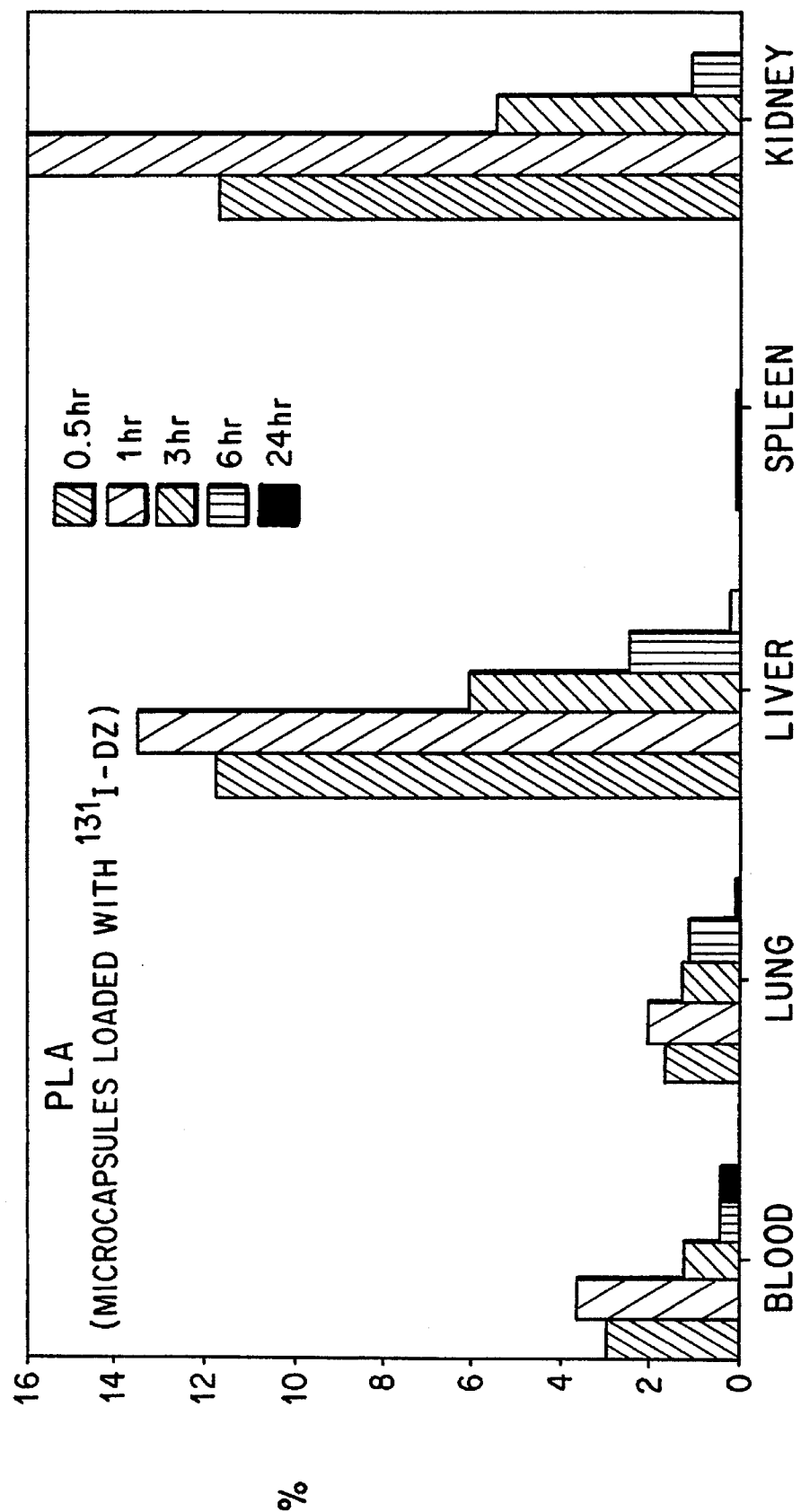

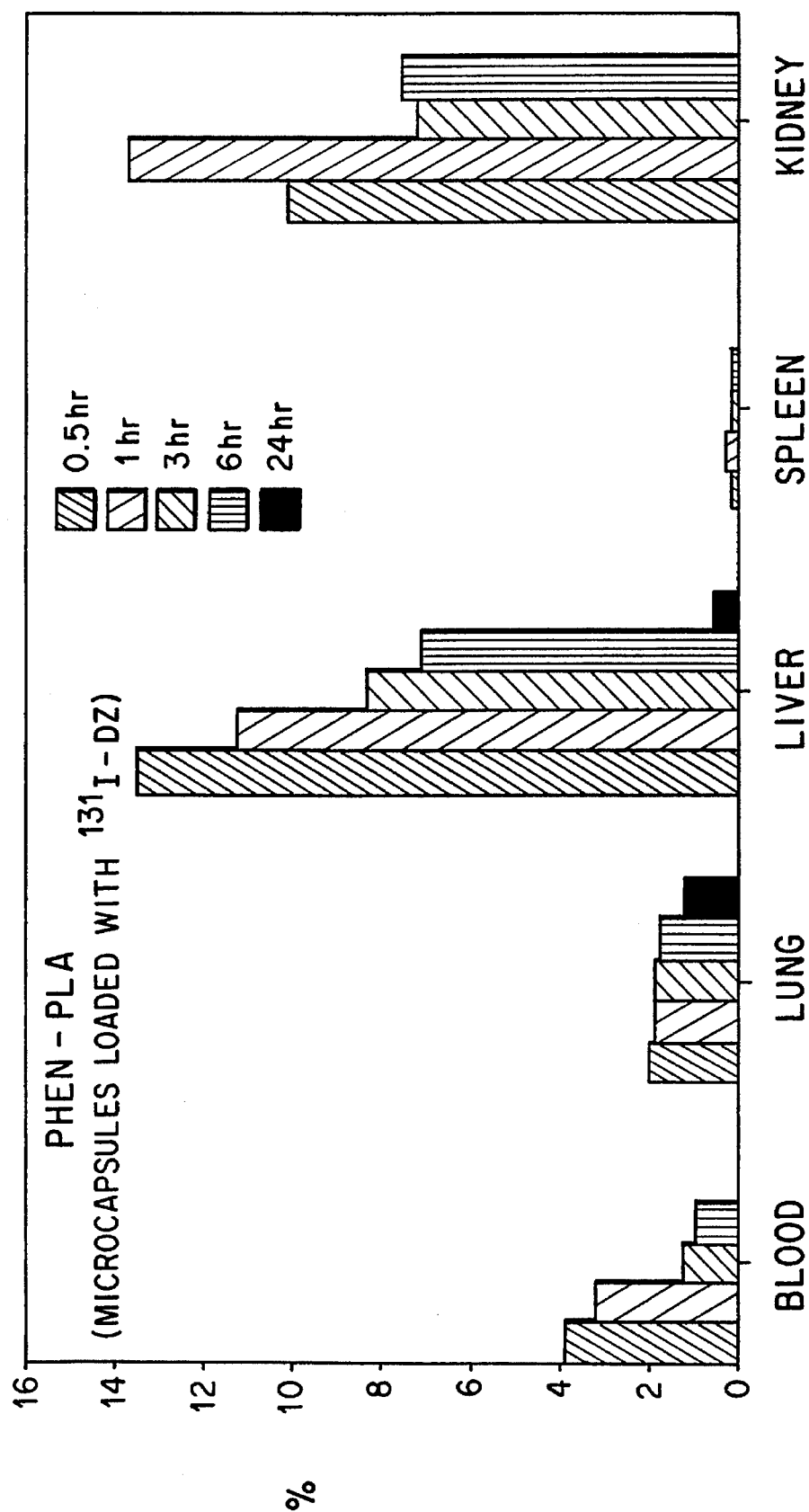

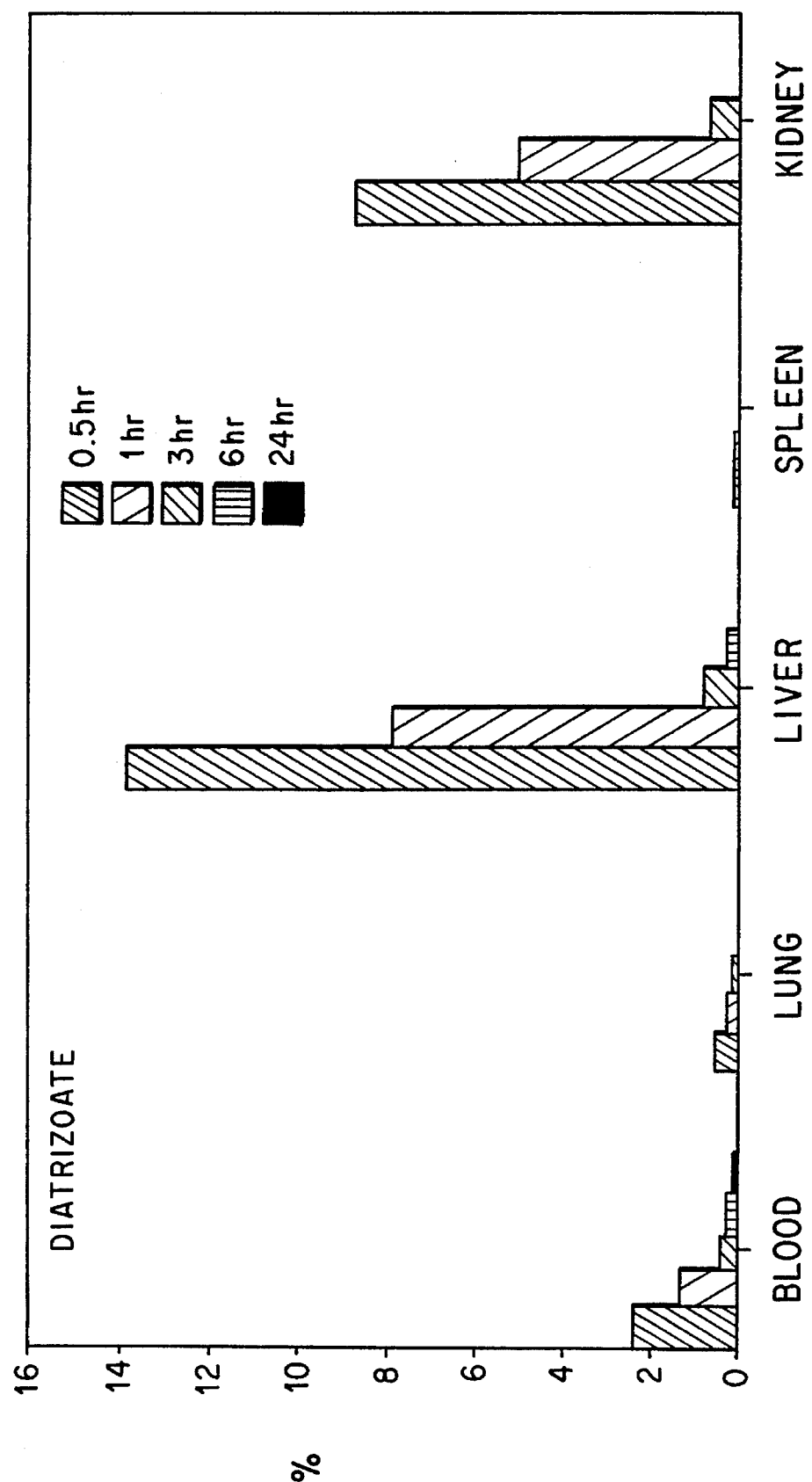

THERAPEUTIC AND DIAGNOSTIC USE OF MODIFIED POLYMERIC MICROCAPSULES

This is a continuation-in-part application of U.S. patent application Ser. No. 07/592,020 filed Oct. 2, 1990, abandoned.

BACKGROUND OF THE INVENTION

1. Field of the Invention

The invention relates generally to a reproducible, efficient method of preparing nonaggregated microcapsules. The microcapsules are suitable for encapsulation or conjugation with substances useful as diagnostic and therapeutic agents. The invention also relates to amino-acid surface modified microcapsules and microcapsules conjugated with agents having particular potential for drug targeting.

2. Description of Related Art

Microencapsulation is a well-studied art. It is basically the use of a matrix or encapsulating material to enclose gases, liquids or solids into particles of relatively small size (nanoparticles up to 500 μm). The matrix is capsular material selected according to the intended use of the microcapsules.

Physical properties of encapsulated chemical entities may be modified because of the encapsulation. Other effects of encapsulation include dispersion of one substance within another, stabilization of emulsions and alteration of solubility rate. One of the most useful properties of encapsulated therapeutic materials is controlled release (Wright, et al., 1989; Wright et al., 1984).

Microcapsules have been prepared by many methods, including coacervation, interfacial polymerization, mechanical methods, polymer dispersion and matrix encapsulation. Sustained release microcapsules have been prepared from ethylcellulose (Kawashima, et al., 1984) and poly-(D,L)-lactide (Benita, et al., 1984). There is voluminous literature on the preparation and use of encapsulating polymers designed for sustained drug release (Bechtel, 1986; Tice, et al., 1989).

Although many preparations of microencapsulated compounds have been reported, few describe microparticles in the size range below 10 μm. Particles of 1–250 μm are typically prepared by a solvent evaporation technique (Tice and Gilley, 1985) while sizes from 1–10 μm have been made by emulsion deposition (Smith and Hunneyball, 1986). One method using solvent evaporation claims to provide a range of sizes from 0.5–250 μm (Mosier, 1985). Nevertheless, none of these methods appears to provide a homogeneous preparation of single-particle, nonaggregated microcapsules. Typical of these preparations is a tendency to aggregate having an overall size of about 177 to 395 μm with 5–162 μm particles making up the aggregates (Jaffe, 1981). This technique requires sieving to remove larger agglomerates, leaving behind a wide range of particle sizes which, although composed of small spheres, are nevertheless in aggregated form.

Discrete microprills, polymeric particles in which a drug (for example, Mellarib™) is uniformly dispersed, have been disclosed (Fong, 1990). Although the microprills were reported to be nonaggregated, the average size range was 10–50 μm.

Lack of particle size homogeneity may cause severe problems in quality control and in clinical use. For example, in chemoembolization studies, the particle diameter is fairly critical in that only a limited range of sizes will lodge in a target area (Bechtel, et al., 1986). If too large, damage to larger vessels may occur, while if too small, the particles pass through and drug is not released at the targeted site. Thus a homogeneous particle preparation is important.

Despite the proliferation of microencapsulation methods, there is a particular need for simple and efficient methods of producing homogeneous preparations of microencapsulated agents for clinical treatment and diagnosis, most particularly in small, nonaggregated particles ranging from 0.5 to 500 μm. A method of preparing encapsulated therapeutic agents in 1 μm and 100 μm particles would provide more effective agents, particularly for diagnostic imaging and chemoembolization.

Bioimaging agents microencapsulated in 1 μm particles would provide an ideal size particle for bioimaging studies, particularly if combined with capsular material selected to concentrate in the organ of interest. Additionally, the use of microencapsulation materials capable of targeting particular areas in vivo would enable improvements in biodistribution imaging studies as well as in drug delivery to specific organs.

SUMMARY OF THE INVENTION

The present invention is a highly efficient, reproducible method of obtaining homogeneous nonaggregated preparations of polymeric microcapsules in which therapeutic or diagnostic agents may be encapsulated or conjugated. The invention also includes microcapsules prepared from polymers conjugated to an amino acid, enabling improved targeting of drug-laden microcapsules to a particular target organ or cell. The invention illustrates two important size ranges, 1 and 100 μm, of polymeric particles useful in clinical studies and in which imaging or therapeutic agents may be efficiently encapsulated.

An important aspect of the invention is the preparation of homogeneous nonaggregated microcapsules having a diameter of approximately 1 μm. These microcapsules are prepared by combining a solution which may contain a drug or therapeutic agent, a nontoxic emulsifier and polymer dissolved in convenient solvent, and then vigorously agitating the mixture. Agitation is performed for a period of time sufficient for the development of microcapsules having a mean diameter below 5 μm. The formation of the microcapsules is monitored periodically, after which the organic solvent is removed and the microcapsules collected.

The nontoxic emulsifier may be selected from several commonly used emulsifiers, for example Tween-80, polyvinyl alcohol, sodium laurylsulfate, Span 20, Lubrol, Triton™ X-100, cetylpyridinium chloride and the like. Thus a wide variety of emulsifiers may be suitable, including anionic, cationic, and non-ionic types.

Likewise, a wide variety of materials may be used for the preparation of the capsules, including nonpolymers such as cholesterol, diglycerol, ethyl cellulose as well as numerous types of polymers. Microcapsules particularly useful for clinical or therapeutic purposes release their contents by erosion, degradation or diffusion. This is not to say that microcapsule polymers used for medical treatment must be biodegradable. For example, relatively permanent implantable drug-containing polymers (e.g., hydrogels) might be used for long-term sustained release in certain applications. Polymers particularly suitable for microencapsulation include poly-(D,L)-lactic acid, ethylhydroxyethyl cellulose, polycaprolactone, polycaprolactone diol, polylysine, polyglycolic acid, polybenzyl-L-glutamic acid, polymaleic acid and the like.

Generally speaking, the emulsifier is soluble in water, while the polymer, typically water insoluble, is dissolved in an appropriate organic solvent. Water immiscible or miscible organic solvents may be used, depending on the nature of the polymer. Examples of solvents include, but are not limited to, acetone, water, ethyl acetate, chloroform, carbon tetrachloride and methylene chloride.

An important step in the preparation of nonaggregated microcapsules less than 5 µm in diameter is the vigorous agitation of the mixture containing polymer, emulsifier and, when desired, a diagnostic or therapeutic agent. Agitation may be carried out by stirring, sonication, or a combination of agitation methods. If stirring alone is used, a speed of approximately 1500 rpms is preferred; however, where 1 µm preparations are desired, it is preferable to use sonication alone or in combination with stirring. If both stirring and sonication are used, sonication at approximately 20 Khz and stirring at 500 rpms are preferred settings. Sonication and stirring are most preferably used simultaneously. Agitation is continued for a period of time sufficient to form individual microcapsules with an average size less than 5 µm, typically at least 5 min and more preferably 10 minutes. Under the general conditions described, somewhat longer periods of time may be required depending on the polymer, the organic solvent used, the volume and concentration of starting material as well as pH and temperature. Microcapsule formation is typically monitored by periodically examining size and shape of the microcapsules as they form in solution. This step is particularly useful when optimizing time and agitating conditions to assure homogeneous preparations in the desired size range. Any method that detects size and shape of the capsules may be used, for example, removal of a drop of the solution and inspection under a light microscope at a magnification of approximately 600 fold.

After the microcapsules have formed, the organic solvent is removed from the mixture. A convenient method, particularly for lower boiling organic solvents, is to stir the reaction mixture at relatively slow rpms, for example about 350 rpm, for a period of several hours until the solvent is completely evaporated. The length of time depends on the type and volume of solvent in addition to other factors related to physical properties. For example, the solvent acetone require about six hours for complete evaporation. Other solvents with lower vapor pressure/higher boiling points may require longer periods of time. Evaporation, in this process, occurs at room temperature, but higher temperatures may be applied when different solvents are used. Monitoring of capsule size and shape continues to be important throughout the evaporation phase to assure that aggregation does not occur.

The microcapsules are collected, after complete evaporation of the organic solvent, preferably by filtration, for example, by filtration through a nylon mesh or other suitable filter that allows smaller particles to pass through while retaining the larger particles. The resulting suspension containing 1 µm microcapsules may then be further processed to isolate and store or use the particles. This is conveniently accomplished by centrifuging the suspension after which any residual organic solvent or emulsifier can be removed by washing either with water or sterile saline. The aqueous layer may then be decanted and the microcapsules resuspended in a liquid for storage or for therapeutic use. When used therapeutically, phosphate buffered saline, pH 7.4 is a most preferred resuspension medium. This method has provided a high yield (99%) of nonaggregated 1 µm particles. The amount of material collected in the nylon sieve is rarely over 1%, and the microparticles prepared by this method are remarkably uniform with a narrow size distribution ranging from 0.5 to 5.0 µm with the highest percentage being approximately 1.0 µm.

These microcapsules may be used to enhance or modify properties of diagnostic or therapeutic agents by virtue of the encapsulation. For example, in order to alter biodistribution properties, an ionic radiographic contrast agent may be encapsulated in a nonionic coat using this microencapsulation process. In the first step of preparing an encapsulated drug, the diagnostic or therapeutic agent is added to a mixture containing an aqueous solution, an emulsifier, and a polymer dissolved in solvent. During microparticle formation, the drug is encapsulated. The yield depends on the material being encapsulated. For example, 1 µm and 100 µm capsules of meglumine diatrizoate have relatively high efficiencies of encapsulation of 66% and 46% by weight respectively. Therapeutic agents (cisplatin, 5-fluorouracil and Tamoxifen) and diagnostic agents (Ethiodol, Iohexol, diatrizoate and Hexabrix) have also been incorporated into 100 µm capsules. Encapsulation is not intended to be limited to these particular drugs and it is envisioned that most therapeutic and diagnostic agents, whether water soluble or insoluble, could be encapsulated by this simple method.

Those skilled in the art will appreciate that this method of encapsulation of therapeutic or diagnostic agents will result in an entrapment of the material, which will be released from the microcapsule at different rates depending on the relative amount of polymer to amount of drug encapsulated. Other factors affecting the rate of release are the chemistry of the compound being encapsulated, the environment into which the microcapsule is being placed, temperature of the environment and the nature or chemical composition of the capsular material. The rate of release of drug will also be determined by the relative ratios of drug to polymer, the type of polymer, and the biodegradability of the polymer.

One µm microencapsulated imaging agents are ideal for diagnostic imaging procedures and are readily prepared by the method of the invention. First, a homogeneous nonaggregated preparation of a 1 µm microencapsulated imaging agent is prepared as previously described. The material may be any standard imaging agent, for example, an iodinated compound such as meglumine diatrizoate. The microencapsulated imaging agent can then be administered to an animal or human, preferably by intra-arterial or intravenous injection. The imaging agent is then detected by appropriate means such as computed tomography or intravenous urography.

The general method used for the preparation of 1 µm microcapsules can also be used to make microcapsules of somewhat larger sizes, for example, 100 µm. Non-aggregated microcapsules having a mean diameter of 100 µm can be prepared by combining a polymer in a solvent with a solution of a nontoxic emulsifier. The mixture is emulsified by stirring at low speed, approximately 350 rpm, while monitoring microcapsule formation. The solvent is then evaporated and the microcapsules collected.

One difference between the procedure for preparing 100 µm microcapsules and preparing 1 µm microcapsules is stirring the mixture of the polymer and the emulsifier at a relatively lower speed when the larger particles are desired. The stirring speed is approximately 350–400 rpm. During the stirring process, the size and shape of the particles in the mixture are monitored, for example, by using a light microscope at approximately 125× magnification. After the desired size range of microcapsules has formed, the organic solvent is removed, preferably by evaporation and simultaneous stirring at room temperature. After collection and drying, the microcapsules are preferably sized. This may be accomplished by passing the particles through various sized filters, for example, first 600 µm mesh, then 600–500 µm mesh, then 500–355 µm mesh, then 355–212 µm mesh, and finally 106 µm mesh. The sieved particles yield a mixture containing size ranges of approximately 106–212 µm. Use of these mesh sizes is for illustration purposes only and, of course, any series of that same general size mesh could be used. In the final step the 106– 212 µm particle mixture is sieved through a 106 µm mesh sieve and the particles that pass through the sieve are discarded. This provides a relatively uniform preparation. Using this method, consistently reproducible yields of approximately 70% of particle sizes in the size range of 100–200 µm have been obtained.

In preparing 100 µm diameter particles, any of a number of polymers may be used, including biodegradable polymers such as poly-(D,L)-lactic acid, ethylhydroxyethyl cellulose, polyhydroxybutyric acid, polycaprolactone, polycaprolactone diol, polylysine, polyglycolic acid or polymaleic acid, polybenzylglutamate, polyhydroxypropylglutamate.

In the initial step of preparing 100 µm microcapsules, a selected polymer is first dissolved in an organic solvent then mixed with emulsifier. The solvents may include methylene chloride, chloroform, carbon tetrachloride, or other solvents in which the polymer is soluble. The emulsifier may be selected from any of a group of nonionic, cationic, or anionic emulsifiers. A nontoxic emulsifier is preferably chosen when the disclosed methods of microcapsule preparation are used to encapsulate therapeutic or diagnostic agents for in vivo use. The selected emulsifiers are preferably solubilized in saline, although water or buffers may be used. Hydrophobic or hydrophilic therapeutic or diagnostic agents may be microencapsulated in the 100–200 µm particles. These compounds generally release slowly from the microcapsules and the rate of release will depend on the nature of the compound encapsulated, as well as the type of polymeric material used for the microcapsules.

It has been found that the 100–200 µm microcapsules are ideal for chemoembolization. When chemoembolization is desired, a drug encapsulated in a biodegradable or nondegradable polymer is prepared. The microcapsule generally has a diameter of about 100 µm which is somewhat larger than the diameter of the tumor vessels in the targeted organ. Encapsulated material is administered intra-arterially causing occlusion of the arteries. By occluding the arterial supply to neoplasms with 100 µm capsules, the ischemia results in death of the tumor cells. The rate of release will depend on the nature of the material used to prepare the microcapsules. Slow release over hours or weeks allows greater contact time between the cytotoxic agents and tumor cell in an anoxic environment which also increases capillary permeability.

Examples of microencapsulated drugs useful for chemoembolization are cisplatin, 5-fluorouracil and Tamoxifen. In one particular example, cisplatin was microencapsulated and administered into canine renal arteries. Poly-(D,L)-lactide capsules and ethylhydroxyethyl cellulose capsules, both loaded with cisplatin, exhibited sustained cisplatin release for at least several days. The resulting tissue destruction was significantly greater than that with blank capsules. These sustained-release properties should be similar for other drugs and other similar polymers.

Normally, drugs or other agents administered to an animal or human will initially disperse through the body before concentrating in the liver, spleen, kidneys and urinary bladder prior to elimination. The inventors have discovered that amino acid ester conjugation to polymers affects the distribution and uptake of the encapsulated imaging material. In a particular example, phenylalanine-conjugated polylactic acid was used to encapsulate meglumine diatrizoate. An animal injected with phenylalanine ester-conjugated encapsulated diatrizoate showed faster liver uptake than animals injected with nonconjugated polymer capsules. In the former case, imaging was possible as early as sixty minutes after injection. Two hours post injection, the nonconjugated microencapsulated material showed both liver and kidney uptake as well as presence in the systemic circulation. In contrast, the conjugated microencapsulated material was concentrated mainly in the liver with little material indicated in the general circulation at two hours post-injection. Both non-conjugated and amino acid-conjugated poly-(D,L)-lactide microencapsulated diatrizoate permitted computed tomography imaging up to three days after administration. Neither material was seen in the liver five days post-administration. In vitro mouse liver cell culture studies confirmed that conjugated microcapsules were mainly taken up by hepatocytes whereas the nonconjugated microcapsules were taken up by Kupffer cells.

Other amino acids conjugated with polymeric encapsulating material are also expected to show selective targeting of encapsulated drugs. Examples include tyrosine, tryptophan, methionine and the like. A selected amino acid may be covalently conjugated to a polymeric material via an amide bond to link phenylalanine with polylactic acid, for example. This is conveniently performed by carbodiimide coupling procedures well known to those experienced in the art; such as reacting with dicyclohexylcarbodiimide in the presence of hydroxysuccinimide. Covalent bonds need not be limited to linkages involving the primary amine of the amino acid but might, where desired, utilize a sulfur-carbon bond between a sulfhydryl-containing amino acid and the polymer. Furthermore, depending on the nature of the functional groups on the polymer, other types of linkages could be formed, for example, ether linkages. Other conjugates are also envisioned; for example, sugars, amino acids or derivatives of these compounds could also be employed to surface-modify a microcapsule polymer.

Surface properties of 100 µm microcapsules may be modified in the same manner as surface properties of the 1 µm microcapsules by conjugating with various amino acids or other surface-modifying materials. In chemoembolization, surface modification would likely be important. These particles could be delivered intra-arterially to the organ of interest.

In many situations, drugs or targeting agents may be conjugated with a selected polymer prior to formation of microcapsules. However, this is not be feasible for some types of targeting agents, including many antibodies or other compounds that might be altered during microcapsule preparation. Such species may be conjugated to surface groups of polymeric material in already formed microcapsules.

Yet another aspect of the invention relates to microcapsules modified by attachment of selected targeting agents. Attachment is typically covalent and the nature of the chemical bond depends on the particular polymer used to prepare the microcapsule. For example, selected agents with amine functionalities may be reacted with carboxyl moieties on a selected polymer using coupling methods well-known to those of skill in the art. Other modifications include for example, creation of "spacers" on either the target molecule or groups on the microcapsule polymer, although such spacer groups are not necessarily required. In a preferred embodiment, poly benzyl-L-glutamic acid polymer is conjugated with estrone, an estrogen-receptor targeting compound. The conjugated material may then be employed for tumor targeting or imaging studies in organs high in estrogen receptors. Such surface modification of microcapsules significantly alters tissue distribution, as demonstrated in the higher uterus-to-muscle ratios achieved with estrone conjugated $^{131}$I-labeled microcapsules compared with the labeled microcapsules alone.

A preferred polymer for conjugation of targeting agents is poly-benzyl-L-glutamic acid. When desired agents are attached to the polymer, an important consideration is the percent of targeting material in the conjugated product. While a high amount may appear desirable, it has been found that substitution is preferably limited to a degree that will permit solubility in a solvent suitable for microcapsule preparation by the disclosed solvent evaporation method. This amount will vary with the nature of the polymer used and with the attached agent. As an example, 12% estrone content in estrone conjugated poly-benzyl-L-glutamic acid microcapsules exhibited good targeting properties while yielding a homogeneous, nonaggregated 1 µm preparation of microcapsules. At high concentrations, an attached targeting agent may adversely affect microcapsule formation.

While conjugation with estrone has been used to demonstrate the targeting properties of conjugated microcapsules prepared in accordance with the invention, it will be appreciated that enhanced targeting is associated with the microcapsules themselves. Thus, in general, the various polymeric microcapsules disclosed may be surface-conjugated with a wide variety of desirable targeting agents including, but not limited to, steroids, antibodies, particularly monoclonal antibodies or epitopic segments or fragments of antibodies, ricin A conjugated compounds, specific targeting drugs such as Tamoxifen, and the like. Further modifications may be made by attaching targeting agents to microcapsules modified with amino acid groups in accordance with preparations herein disclosed.

BRIEF DESCRIPTION OF THE DRAWINGS

FIG. 20 shows the results of uptake of $^{18}$F-labeled tamoxifen by pig uterus as measured by PET.

FIG. 21 shows the reaction scheme for the preparation of poly(hydroxylpropyl glutamate) and polyhydroxypropyl microspheres employing aminopropyl alcohol modification of PBLG microspheres. FIG. 21A shows the preparation of pHPG microspheres from PBLG. FIG. 21B shows how PBLG microspheres can be reacted with tyramine aminopropylalcohol to form phenol conjugates which readily react with iodine. Labelled microcapsules may be formed using Iodogen-$^{131}$I.

FIG. 22 shows the distribution of polylactate microcapsules labeled with diatrizoate (panel A), phenylalanine conjugated polylactate microcapsules labeled with diatrizoate (panel B) and diatrizoate (panel C), in blood, lung, liver, spleen and kidney after the indicated intervals.

DETAILED DESCRIPTION OF PREFERRED EMBODIMENTS

Figure 1:
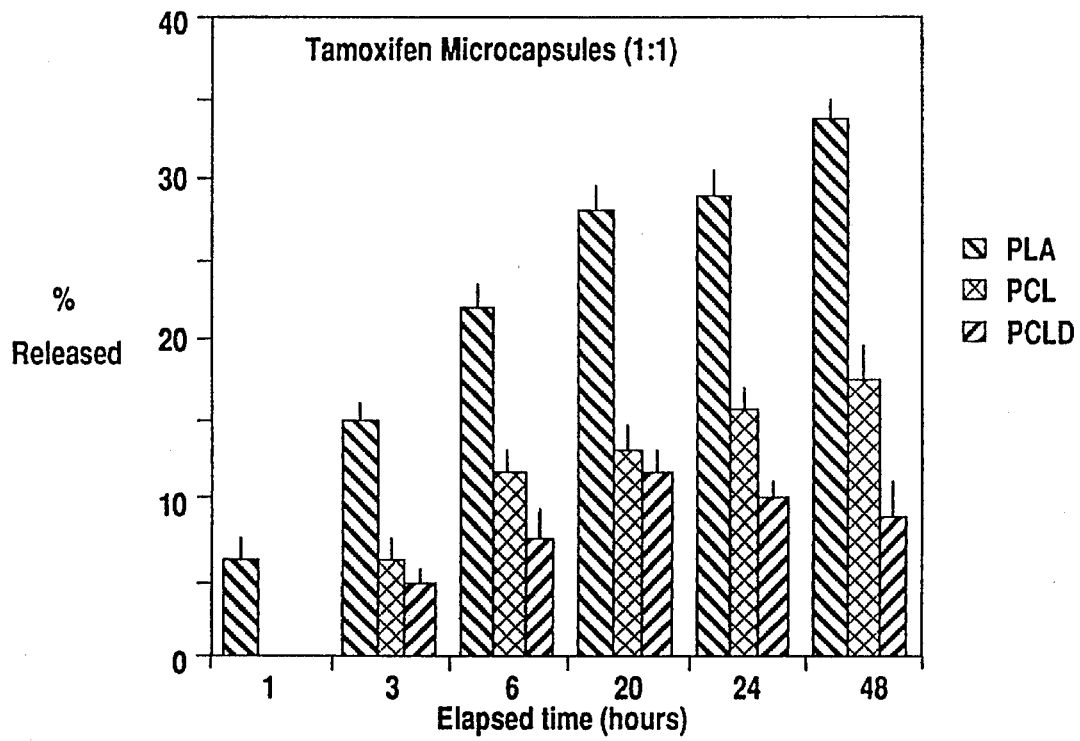
FIG. 1 shows the in vitro profile of Tamoxifen from Tamoxifen microcapsules with Tamoxifen:polymer ratios of 1:1. A statistically significant difference from the corresponding sample after 1 hr of incubation (p<0.05 by Student T-test) was determined. Each bar represents the mean±standard deviation of three samples.

The invention is a method of preparing microencapsulated therapeutic and diagnostic agents in discrete nonaggregated particles suitable for diagnostic radiologic studies and therapeutic use in humans. The novel microcapsules of the invention are useful for selective targeting in vivo because of the modified surface characteristics. In one aspect, the invention is the preparation of hydrophilic microcapsules to which a wide variety of drugs may be attached and which target to sites other than the liver. The method also relates to the preparation of 1 μm particles for intravenous and intra-arterial administration as well as 100 μm particles for intra-arterial use. In other aspects of the invention, cells in the body are specifically targeted with drugs microencapsulated in polymeric material whose surface properties are modified by conjugation with an amino acid. The microcapsules may be conjugated or used to encapsulate targeting agents which bind to specific body cell receptors, including steroids, antibodies and the like.

Materials and Methods

Poly(benzyl-L-glutamate) of two average molecular weights (MW 58,000 and 43,000) was obtained from Sigma Chemical Co. (St. Louis, Mo.). Poly-(D,L)-(lactic acid), was obtained from Polysciences, Inc. (Warrington, Pa.). Cisplatin and estrone were also supplied by Sigma as powders of unspecified size. To prepare cisplatin-containing microcapsules, the cisplatin crystals were ground manually with a pestle in a mortar to an average size of about 3 μm.

Polyvinyl alcohol (MW 30,000–70,000) was obtained from Sigma and used as an emulsifier as received. Chempure™ methylene chloride solvent supplied by Curtin Matheson Scientific, Inc. (Houston, Tex.), was used without further purification. Iopanoic acid was purchased from Sigma and converted to ethyliopanoate for radiolabeling. Radiotracer: [$^{131}$I]sodium iodide (specific activity 7.75 Ci/mg, 680 mCi/ml) was obtained from Dupont New England Nuclear (Boston, Mass.). Rats: Female rats weighing 100–125 g were purchased from Harlan Sprague-Dawley, Inc. (Indianapolis, Ind.).

Large Microcapsule (100–200 μm) Preparation

Drug-loaded capsules were produced by the solvent-evaporation procedure according to Example 1. Various amounts of cisplatin and poly(benzyl-L-glutamate) were dispersed in methylene chloride depending on the drug-to-polymer ratio desired. The cisplatin: PBLG ratios were 2:1 (0.8 g:0.4 g), 1:1 (0.5 g:0.5 g), 1:1.5 (0.33 g:0.5 g), and 1:2 (0.4 g:0.8 g). The cisplatin crystals were ground with a mortar and pestle for 5 minutes before being weighed. The appropriate amounts of drug and polymer were then stirred for 20 minutes or more in 5–20 ml of methylene chloride. This organic phase was emulsified in 250 ml of water containing 2% (w/v) polyvinyl alcohol spun at 350 rpm. The resulting mixture was stirred for 5 hours at room temperature (24° C.) to ensure complete evaporation of the solvent. The contents of the beaker were then poured through a Buchner funnel under suction. The microcapsules remaining on the filter paper were washed with 250 ml of water to remove the emulsifier. Cisplatin crystals were left on the filter to air dry. Microcapsules were collected using a sieve to separate the 100–200 μm fraction.

Determination of Cisplatin Content

Ten milligrams of each batch of capsules was dissolved in 5 ml of N,N-dimethylformamide (Fisher Scientific Co., Fiar Law, N.J.). The amount of cisplatin in the resulting solution was determined using a Perkin Elmer model 55 ultraviolet spectrophotometer (Coleman Instruments Division, Oakbrook, Ill.) at 310 nm. A standard curve was produced using the same procedure by adding a known amount of pure cisplatin (5 mg). Experiments were performed in triplicate. The drug content was calculated as a percentage of the total weight of the capsule.

In Vitro Sustained Release

Because of variations in the yield of each batch of capsules after sieving, release rates were run in triplicate. Thirty milligrams of capsules were weighted into VACUTAINER brand evacuated blood collection tubes, 10 ml draw (Becton Dickinson VACUTAINER Systems, Rutherford, N.J.), and 5 ml of Dulbecco's phosphate buffered saline (PBS) without calcium or magnesium (Sigma Chemical Co.) was added. Initially, the tubes were inverted several times to ensure contact of the capsules to the PBS (pH 7.4). The test tubes were immersed in a water bath at 37° C. and shaken on a water bath.

Tubes were periodically centrifuged at 2500 rpms for 5 minutes and 3 ml of the PBS drawn off and analyzed using ultraviolet spectrophotometry. The remaining 2 ml of solution was removed and 5 ml of fresh PBS added for each measurement. Tubes were inverted several times before returning to the shaker bath. The effects of centrifugation on capsule morphology were examined using cross-sections of capsules centrifuged for six 5-minute intervals.

Microscopy Studies

Surface characteristics of the microcapsules were evaluated using a scanning electron microscope. One micrometer cross sections of the capsules were obtained and embedded in EPON, a Medcast resin (Ted Pella, Inc., Redding, Calif.), cast in BEEM imbedding capsules (Ted Pella), and cut on a microtome. Cross sections were photographed with an Axiovert 405M inverted photomicroscope (Zeiss, Germany) equipped with a long distance condenser for differential-interference contrast and a 35 mm camera.

Radiolabeling of Ethyl Iopanoate 2 g (3.5 mmol) of iopanoic acid was dissolved in 50 ml absolute ethanol, and 0.4 ml (5,25 mmol) thionyl chloride was added. The reaction was refluxed for 3 hours. After cooling, the reaction mixture was evaporated and reconstituted in 100 ml methylene chloride. The organic mixture was washed twice with 25 ml 5% NaOH and twice with 25 ml water. The methylene chloride layer was dried over $MgSO_4$ and evaporated to dryness, yielding 1.73 g of ethyliopanoate (82.4%). The structure was provided by $^1H$ nuclear magnetic resonance and mass spectrometry ($M^+$ 599). The radioisotope exchange reaction was carried out using a known procedure with some modification (Zupon, et al., 1983; Kroschwitz, 1989). Briefly, 10 mg of the ester and 0.3 ml of tetrahydrofuran were placed in a vial and treated with 1.6 mCi of [$^{131}I$]sodium iodide (in 100 μl of 0.1M sodium borate buffer). Pivalic acid (25 mg) was then added. The reaction vial was sealed and heated at 150° C. for 1.5 hours. The vial was cooled and the ethyliopanoate reconstituted in methylene chloride (0.1 ml) and chromatographed on a silica gel column with methylene chloride/methanol (9:1) as the eluent. This yielded 0.54 mCi ethyliopanoate (34%). Radiochemical purity was determined by co-chromatography on a silica gel plate eluted with methylene chloride methanol (9:1); unlabeled ester served as the standard, with a retardation factor of 0.80.

In Vivo Tissue Distribution

PBLG and estrone-PBLG microcapsules loaded with [$^{131}I$]ethyliopanoate (5.7 μCi in 0.6 ml of water) were administered to rats in the tail vein. Rats (N=3/group) were sacrificed at 1, 3, 6, and 24 hours after injection. The percentage of injected dose in an organ or tissue was determined by a gamma counter.

Positron Emission Tomographic Evaluation of PBLG Microcapsules

Positron emission tomography (PET) imaging was performed on four domestic female pigs (30 lb) with a positron camera (Positron Corp., Houston, Tex.). A 20-minute attenuation scan was performed with a 4-mCi $^{68}Ge$-ring source prior to tracer injection. After each pig received 10 mCi of $^{18}F$-labelled tamoxifen, eight consecutive 10-minute scans were performed employing a 5-minute wait between scans for data transfer. Total counts collected per scan was 15–30 million. Serial transaxial images of the pelvic region enabled viewing of the uterus. The tomograph has a field of view of 42 cm on the transverse plane and 12 cm on the coronal plane. The axial resolution on the reconstructed plane is 1.2 cm. Twenty-one transaxial slices separated by 5.2 mm were reconstructed for each scan.

Each pig was supine in the scanner to allow the detector rings to span the entire pelvic region. Prior to scanning, the position of the uterus and ovaries was determined by hysterosalpingography. Fifteen milliliters of radiopaque (Renografin 76, Squibb Diagnostic, New Brunswick, N.J.) was injected through the vagina into the uterus through a 5 Fr catheter whose balloon was inflated by 1 ml of air. Radiographs of the pelvis in the anterior-posterior position were taken. The location of the uterus was marked permanently on the skin of each pig for consistent positioning in the PET camera. The same positioning was used in subsequent scanning.

To demonstrate that the estrone-PBLG uptake in the uterus and ovaries was effected by estrogen receptors, a pig was given estrone-PBLG (200 mg) empty capsules 30 minutes before intravenous injection of the [$^{18}F$]-labelled tamoxifen (Yang, et al., 1991)

Morphology and Release Pattern of Large Microcapsules

Cisplatin-containing capsules of 100–200 μm prepared by the process described herein were appropriate for in vivo use as determined by gas chromatography, mass spectrometry with a mass selective detector. The amount of residual methylene chloride in the capsules was less than 0.2 ppm.

Figure 17A:
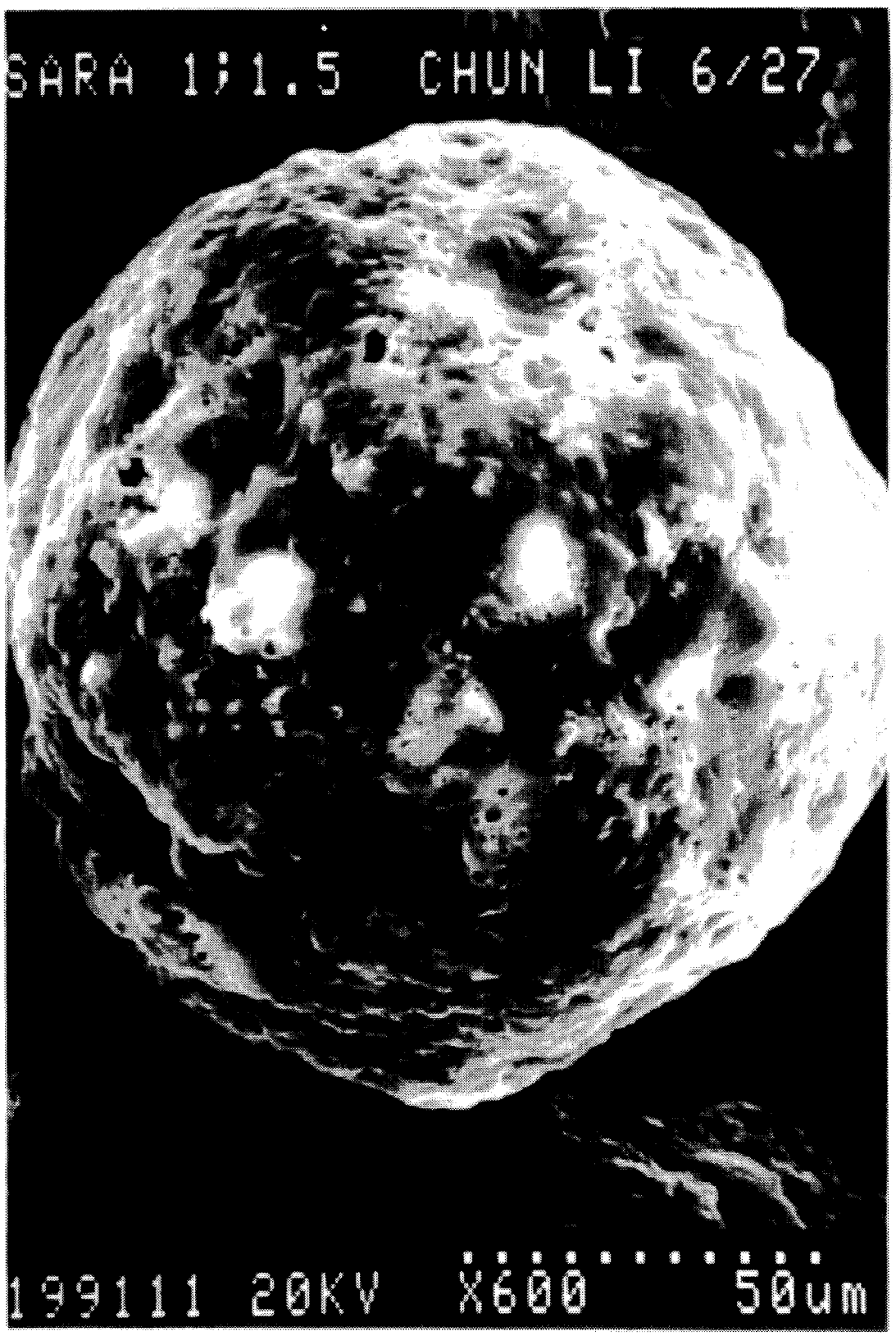
FIG. 17A is a scanning electron micrograph of batch 1 cisplatin-loaded PBLG capsules (100–200 µm), 29.2% (w/w) drug loading, 1:1.5 drug-to-polymer ratio; 17B shows an optical micrographs of cross-sections of PBLG 250µ microcapsules, 2:1 drug-to-polymer ratio, 37.5% drug loading.
Figure 17B:
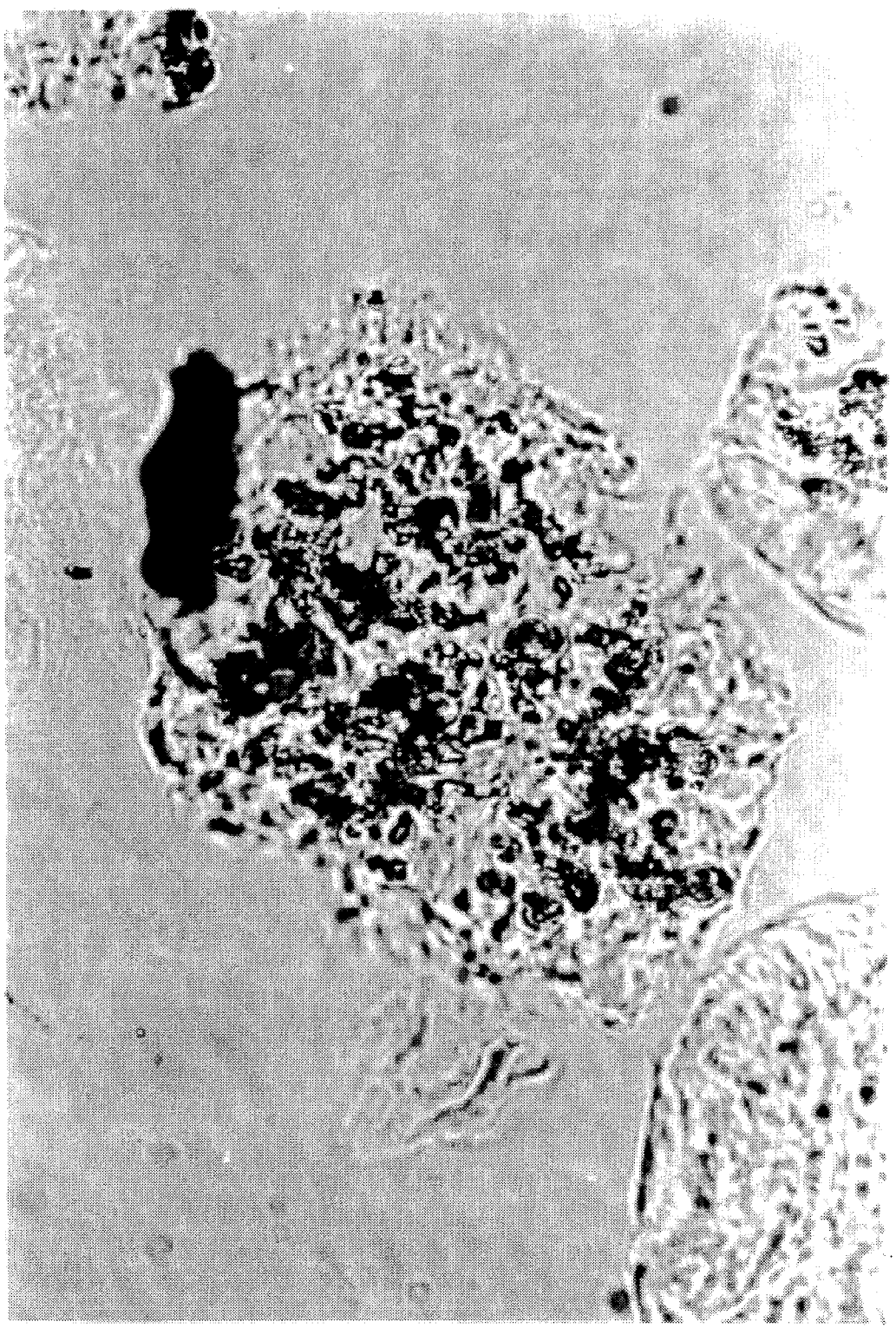
FIG. 17 shows micrographs of cis-platin loaded PBLG (poly benzyl-L-glutamate) microcapsules.

Scanning electron microscopy showed that almost all the drug was encapsulated, regardless of the drug-to-polymer ratio. All the capsules had porous outer surfaces (FIGS. 17A and 17B). Processing conditions and experimental loading yields are given in Table 1. The efficiency of drug loading in the microcapsule prepared is clearly influenced by the viscosity of the organic phase.

Figure 18:
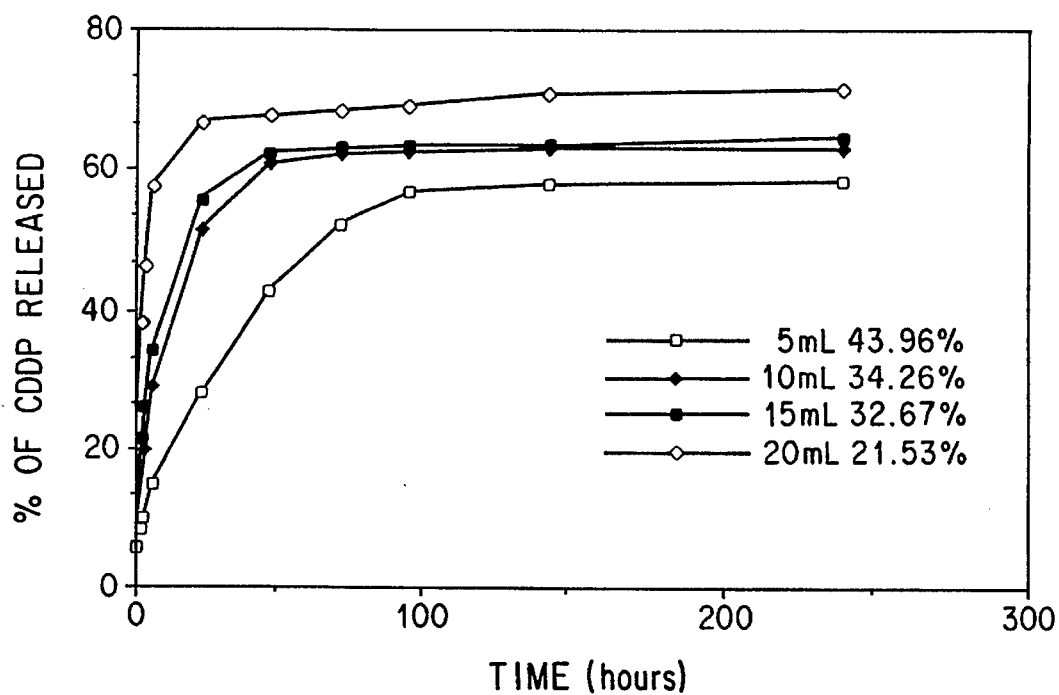
FIG. 18 shows the effect of drug loading after viscosity changes in the organic phase on the cisplatin release rate from cisplatin-PBLG microcapsules into phosphate buffered saline (PBS) solution.

The factors affecting drug loading also direct the release rates of microcapsules. FIG. 18 indicates that higher loading due to increased viscosity of the organic phase causes capsules to release their drug load more slowly. Microcapsules with a 21.53% drug load (20 ml $CH_2Cl_2$) exhibited a strong initial release and continued to release rapidly for the first 24 hours. At 43.96% loading, the microcapsules prepared with 5 ml of methylene chloride released in a slower, more linear fashion and did not reach a release plateau until after 96 hours. The difference between the two release rates was especially striking during the first hour. The lower loaded capsule (21.53%) released 26.0% of its load within the first hour of being introduced to the PBS; however, the capsule bearing 43.96% drug lost only 5.8% of its drug load under the same conditions.

Figure 19:
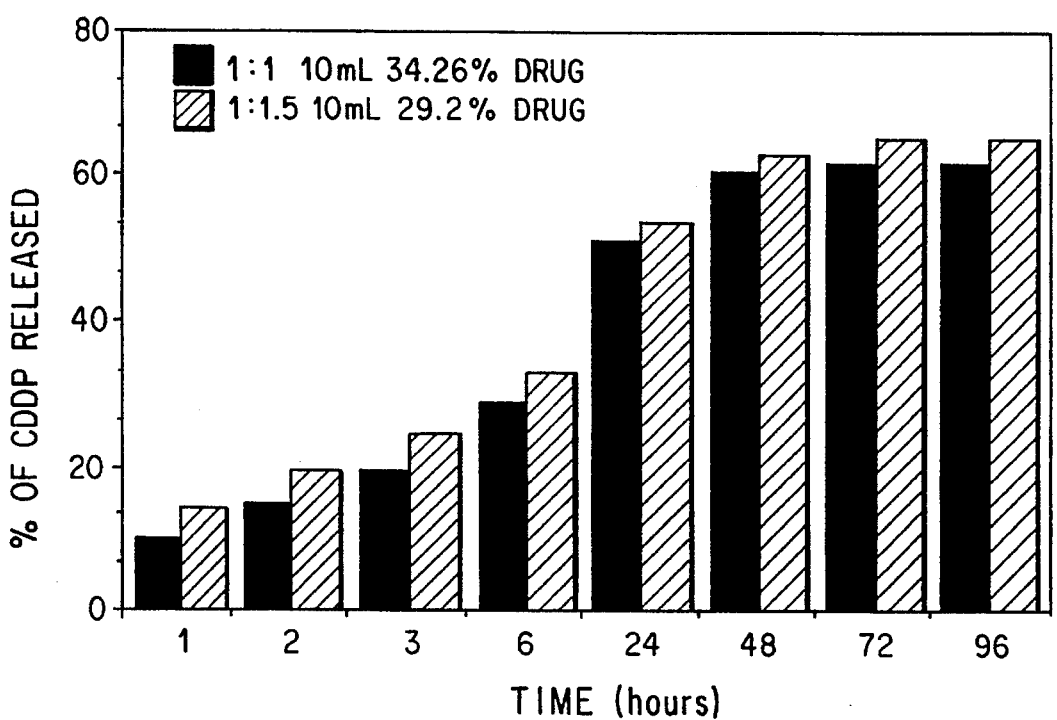
FIG. 19 shows the effect of drug loading on the rate of cisplatin release from cisplatin-PBLG microcapsules into PBS solution. Results for two different preparations (solid bar) and (hatched bar) are shown.

As seen in FIG. 19, the capsule with higher loading resulting from a higher core-to-wall ratio, also released more slowly, even though the amounts of methylene chloride used in preparation of the capsules were the same. All capsules displayed the same general release pattern: an immediate strong release that tapered off within the first 1 to 4 days. The loading affected only the strength and duration of the initial release. In no case was there any indication of degradation of the polymer matrix such as would be indicated by a delay of several days before drug release or a sudden increase in drug release.

The processing conditions described herein yield PBLG-cisplatin microcapsules in which higher drug loading corresponds to more central drug concentration and slower release rates. However, all capsules prepared demonstrated sustained-release properties during 31 days of monitoring without an initial or final burst that would complicate their clinical use as a means of steady drug administration.

In Vitro Estrogen Receptor Assay of Estrone-PBLG Conjugates

Scatchard analysis of [$^3H$]estradiol binding in pig uteri indicated a single class of binding sites with a mean binding affinity constant (kd) of 2.2 nM and a mean receptor density (βmax) of 350 fmol/mg protein. The protein concentration used was 1 mg/ml cytosol. Hill analysis (coefficient 0.992) indicated that estradiol has competitive reversible binding. The $IC_{50}$ for estrone was $5\times10^{-8}$M and for estrone-PBLG was $5\times10^{-7}$M (based 12% conjugation).

In Vivo Tissue Distribution of Small Microcapsules

The results of tissue distribution studies for $^{131}$I-labeled microcapsule groups are shown in Tables 2 and 3. The uterus-to-muscle radioactivity-uptake ratio in the estrone-PBLG group was higher than that of the PBLG group.

PET Studies of small Microcapsules

Figure 20A:
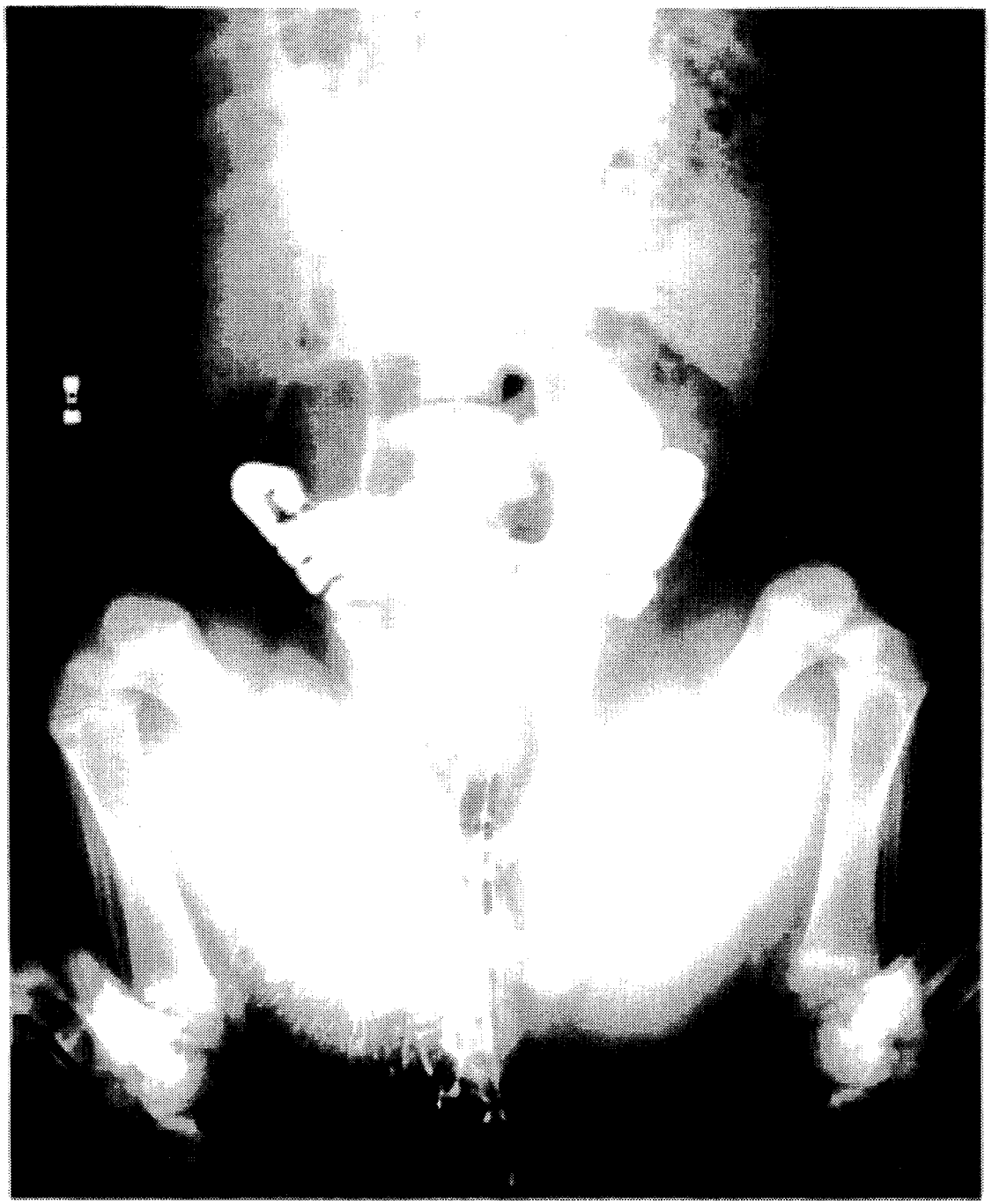
FIG. 20A is a radiograph of a pig's pelvic region. The bright site is the uterus.
Figure 20B:
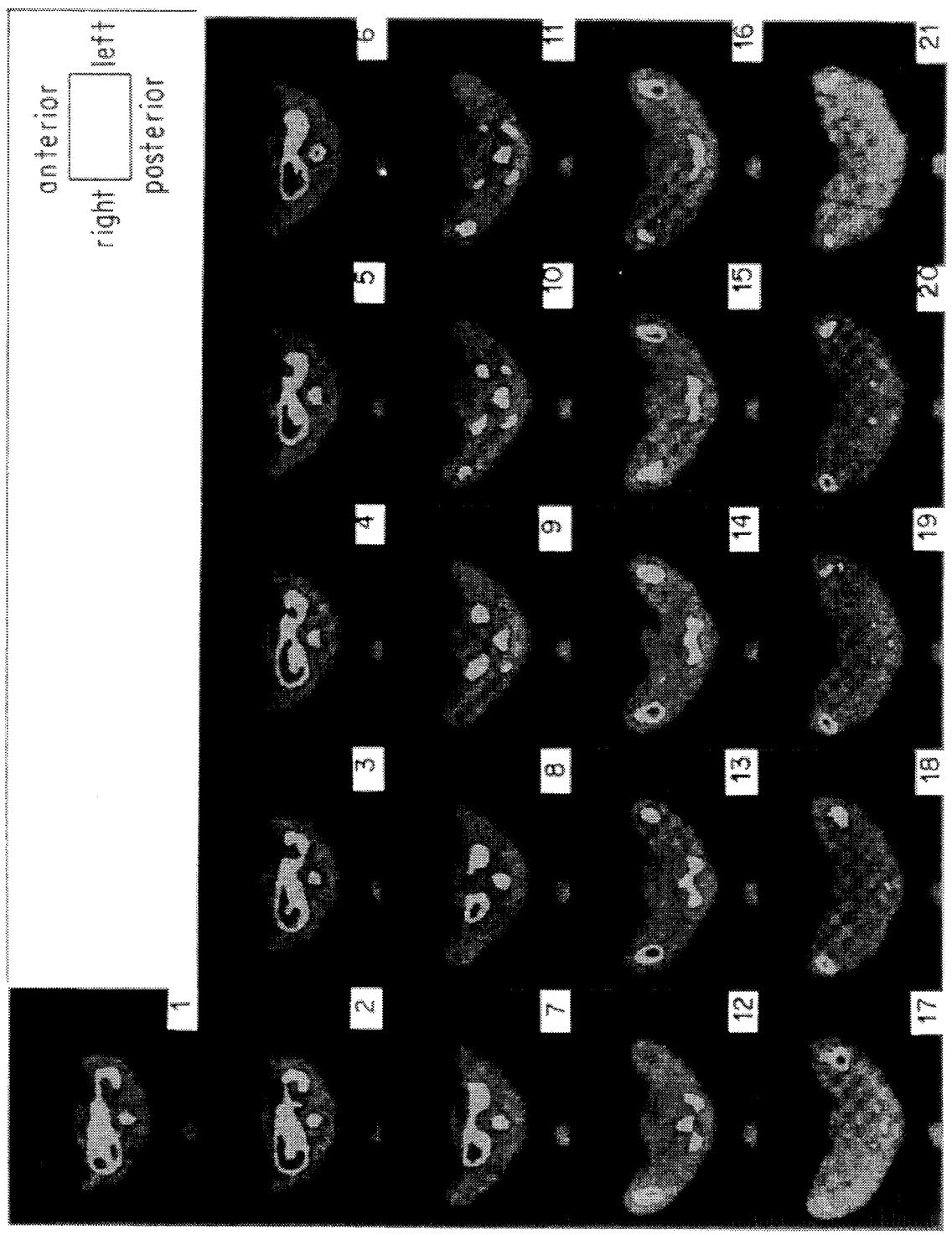
FIG. 20B is a PET image of the pelvic region of a pig receiving the $^{18}$F-labelled tamoxifen.
Figure 20C:
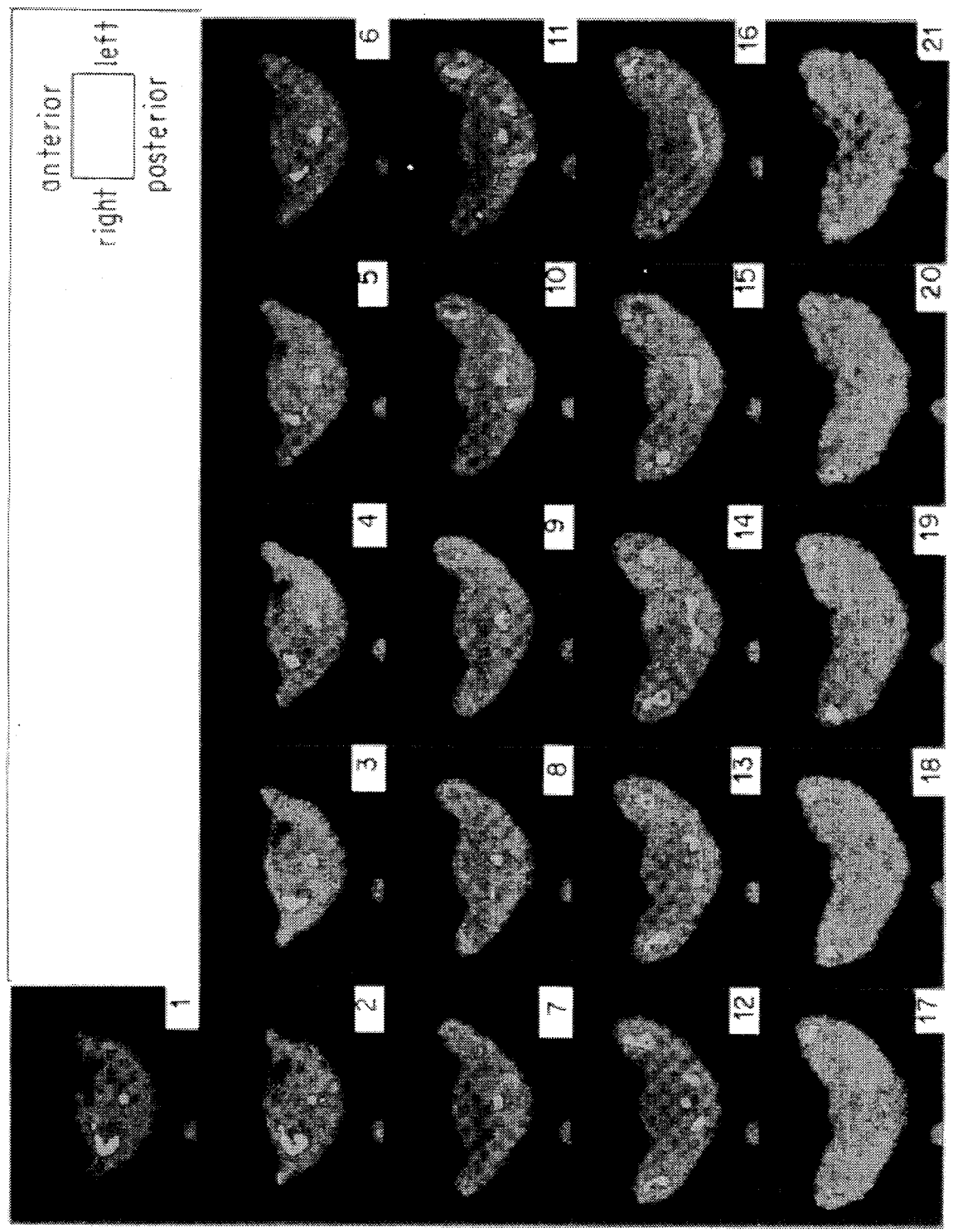
FIG. 20C indicates that uptake in the uterus was blocked after pretreatment with estrone-PBLG (200 mg) empty particles. The image was obtained 1 hour after injection of the $^{18}$F-labelled tamoxifen.

The PET image was correlated with the findings on the hysterosalpingogram. FIG. 20A is the transaxial view of a PET image of the pelvis of a pig 1 hour after administration of $^{18}$F-labeled tamoxifen. The pig was scanned in a caudal-to-cranial direction. Slices 2–6 showed increased tamoxifen uptake in the uterus and ovaries (FIG. 20B). This increased uptake was blocked by pretreatment with estrone-PBLG (200 mg) empty capsules (FIG. 20C). Slices 2–6 show the effect of this blockage. Here, the pig was scanned in a cranial-to-caudal direction. The PET data indicate that the uptake of estrone-PBLG microcapsules in the uterus and ovaries was mediated by means of estrogen receptors.

The following examples are intended to illustrate specific embodiments of the present invention. Those skilled in this field will recognize that modifications could be made to the disclosed methods and that other applications would remain within the scope of the present invention.

EXAMPLE 1

100 Micron Microcapsule Preparation of Microencapsulated Meglumine Diatrizoate Meglumine diatrizoate, 2 g, was dispersed in 40 ml methylene chloride and 1 g poly-(D,L)-lactic acid added to the mixture. Encapsulation was achieved while stirring at 350 rpm in 250 ml 0.9% (w/v) saline solution containing 1.25 g polyvinyl alcohol. The pH of the solution was adjusted below 4 with 1N HCl. From time to time, formation of microcapsules was determined by examining a drop of the material at 125× magnification under a light microscope. The mixture was stirred for approximately 6 hr until the methylene chloride was completely evaporated. The microcapsules were collected by filtration and washed with distilled water (2×100 ml). The microcapsules were air dried at room temperature and then sieved through various meshes, including stepwise, 600 μm mesh, 600–500 μm mesh, 500–355 μm mesh, 355–212 μm mesh and 106 μm mesh, to give a mixture containing particles of size range 106–212 μm. The weight of the 106–212 μm particles was approximately 70% of the initial total amount of the contrast agent plus polymer. The microcapsules contained 46% (w/w) of meglumine diatrizoate.

EXAMPLE 2

1 Micron Microcapsule Preparation of Microencapsulated Meglumine Diatrizoate All the following steps were done under aseptic conditions using ultraviolet light with sterile instrumentation.

Figure 7B:
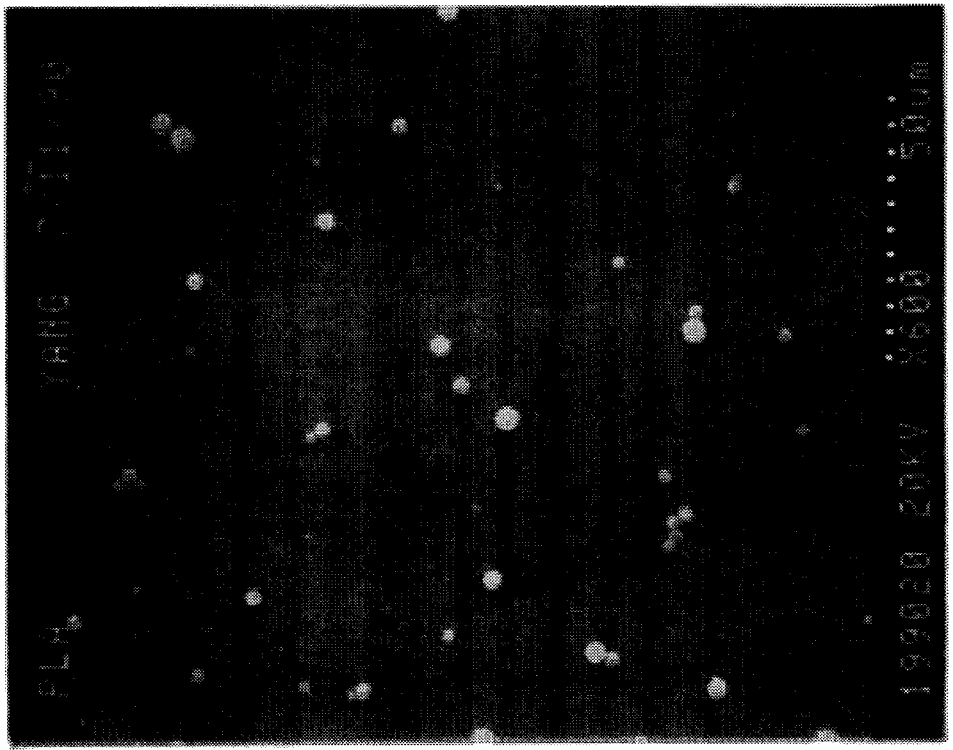
FIG. 7 is a scanning electron micrograph of 1 µm PLA microcapsules (7B) and PLA microcapsules encapsulating meglumine diatrizoate (7A) polymer Drug to ratios were 1:3.
Figure 7A:
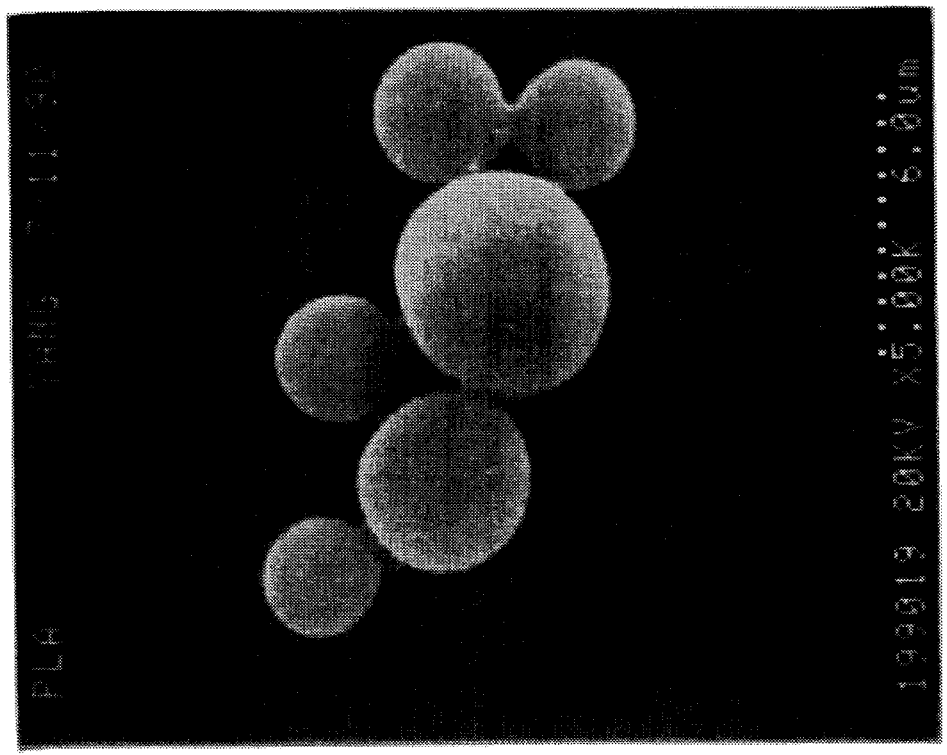
Figure 8:
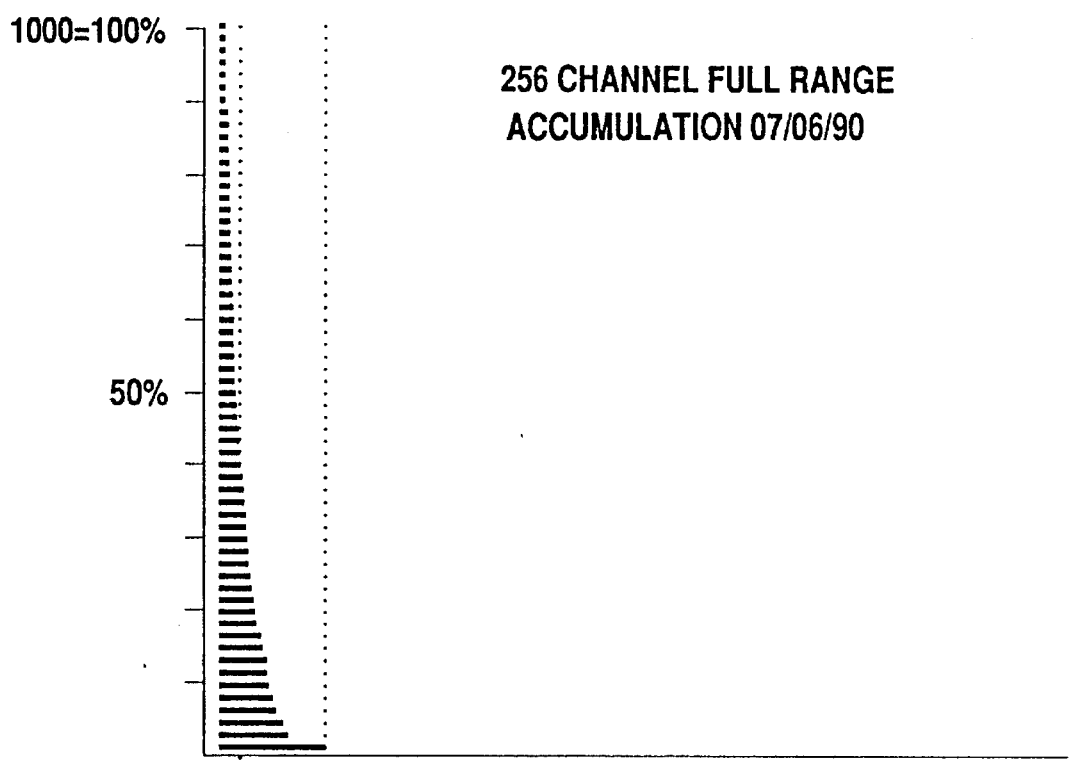
FIG. 8 is a microcapsule size distribution curve with data taken from Coulter Counter measurements. Polylactic acid microcapsules were loaded with meglumine diatrizoate.

Meglumine diatrizoate, 1.2 g (Sigma Chemical Company, St Louis, Mo.), was dissolved in 100 ml water and then 1 ml of Tween 80 was added. The mixture was stirred at 500 rpm and the pH of the solution adjusted below 4 with 1N HCl. To this mixture was added dropwise 0.5 g poly-(D,L)-lactic acid (MW 30,000–60,000) dissolved in 10 ml acetone. The mixture was stirred at 1500 rpm or sonicated at 20 Khz for 10 min and periodically monitored under a light microscope at 600× magnification until round particles of approximately 1 μm in diameter were observed. The mixture was stirred at 1500 rpm (without sonication) or 500 rpm (with sonication) for an additional 6 hr or until the acetone was completely evaporated. The microcapsules were collected by sieving through a nylon mesh to remove a small amount of aggregated material, approximately 1%. The microcapsule suspension was centrifuged at 24,000 g and washed 3 times with saline to remove the emulsifier. The microcapsules were resuspended in sterile phosphate buffered saline. The microcapsules weighed 1.5 g (90% by total initial weight of contrast plus polymer). The microcapsules contained 66% by weight of meglumine diatrizoate. The particles were cultured and found to be sterile. Scanning electron microscopy (SEM) revealed round, uniform particles as shown in FIG. 7. The distribution of particles was determined using a Coulter counter, indicating a narrow range of 2–7 μm with 50% having a mean capsular size less than 5 μm, as indicated in FIG. 8.

EXAMPLE 3

Conjugation of Amino Acid Ester to Polylactic Acid

To a solution of 2.0 g (0.05 mmol) poly-(D,L)-lactic acid in 10 ml dimethylformamide (DMF) was added 1.2 g (5.5 mmol) of dicyclohexylcarbodiimide and 0.68 g (5.5 mmol) of N-hydroxysuccinimide. After stirring 10 min, 1.2 g (5 mmol) phenylalanine ester dissolved in 5 ml DMF was added. The mixture was stirred overnight. The solid urea was filtered. The filtrate was poured into 100 ml water and the white solid precipitated. The solid was filtered, washed with 100 ml water, air dried and weighed to obtain 2.4 g (75%) of the total chemical yield. Thin layer chromatography indicated a single spot (Rf= 0.3, chloroform/methanol 9:1). The phenylalanine content in the polymer conjugate was 23% as determined by ultraviolet spectroscopy at 254 nm. Similar conditions were used to prepare microcapsules of poly-(D,L)-lactic acid conjugated with methionine, tyrosine or tryptophan ester.

EXAMPLE 4

Chemoembolization with Microencapsulated Cisplatin

Eighteen adult mongrel dogs were anesthetized with intravenous sodium pentobarbital (Nembutal; Abbott, North Chicago, Ill.), 30 mg/kg, and an intravenous drip of normal saline was initiated. Through a cutdown, a 5-F polyethylene catheter was introduced into the femoral artery, and the animal was given an intra-arterial bolus of sodium heparin (100 units/kg). The catheter was then advanced into one of the renal arteries. The ipsilateral renal vein was also catheterized via a femoral vein with a 5-F catheter to sample blood for cisplatin (CDDP), while simultaneous systemic venous blood samples were collected through an 18-gauge Cathlon™ catheter inserted in a jugular vein.

Figure 13:
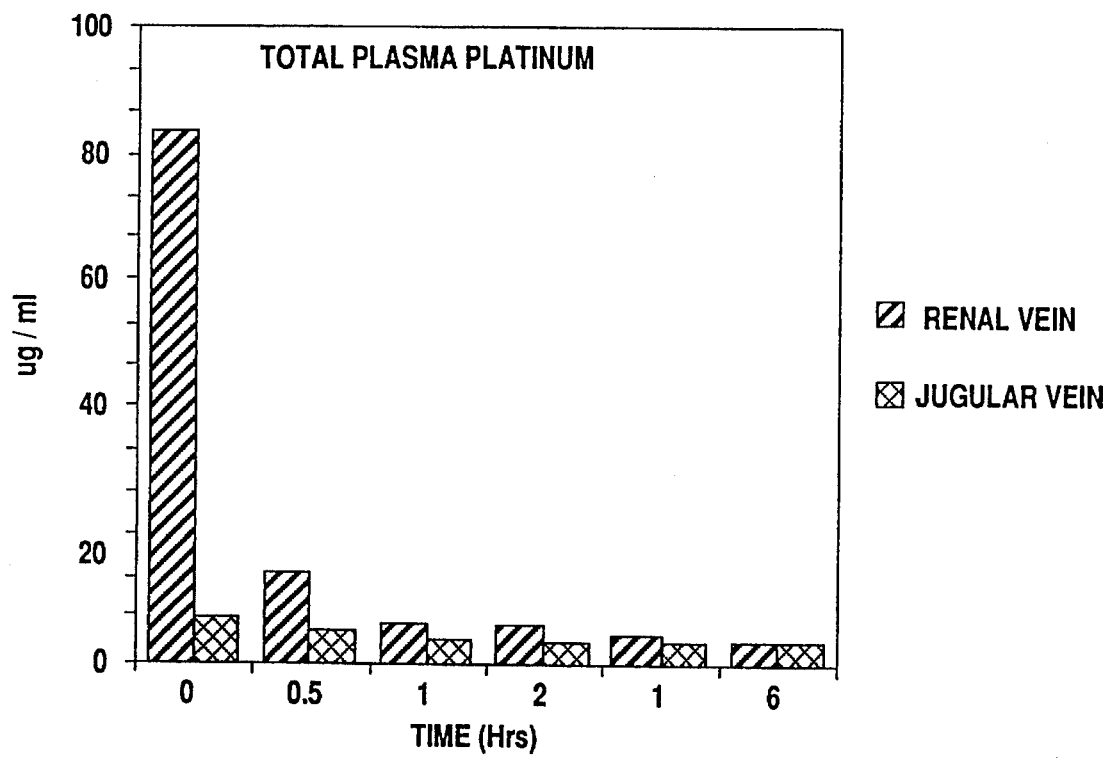
FIG. 13 shows the release rate of CDDP from 100 µm polylactide capsules as measured in jugular and renal vein plasma in dogs at selected times over a period of 6 hours. The drug was administered intra-arterially into the renal artery.
Figure 14:
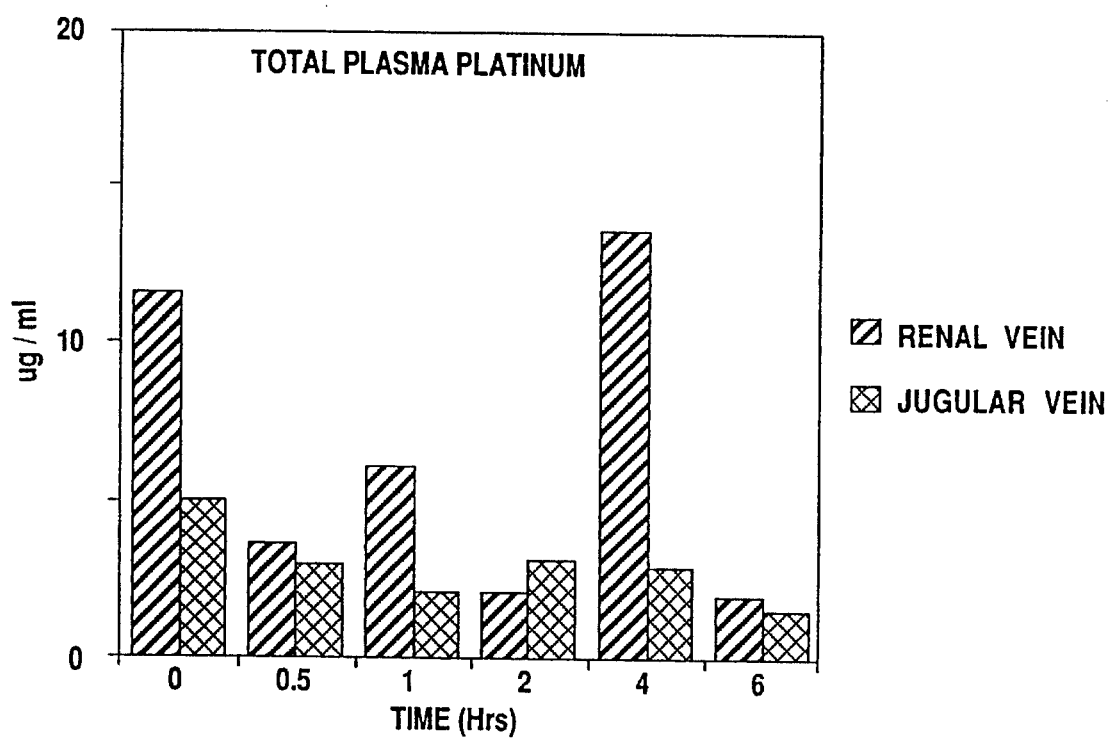
FIG. 14 shows the release rate of CDDP from 100 µm EHEC capsules as measured in jugular and renal vein plasma from dogs at selected times over a period of 6 hours. The drug was administered intra-arterially into the renal artery.
Figure 15A:
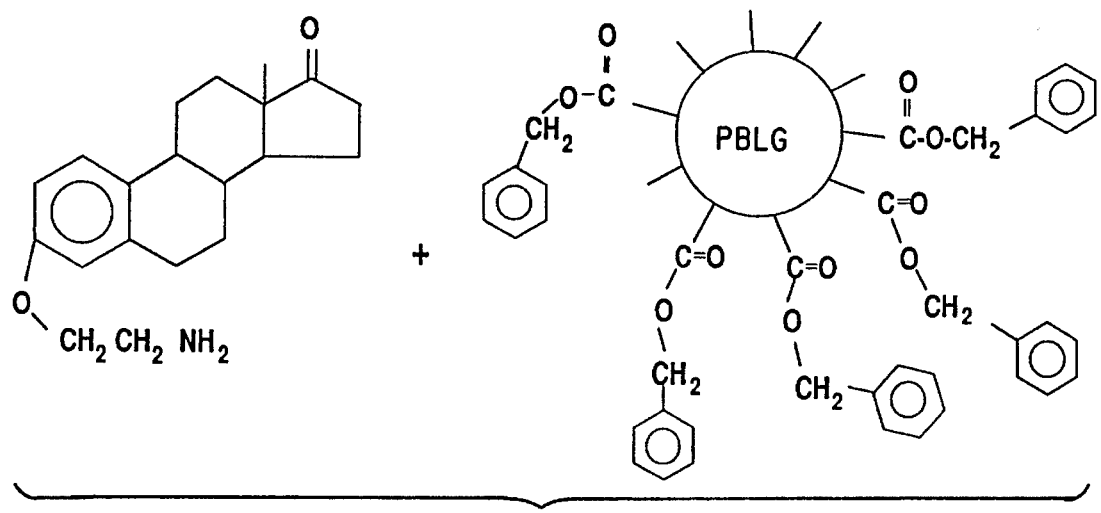
FIG. 15 schematically illustrates the coupling reaction between estrone and poly-benzyl-L-glutamic acid.
Figure 15B:
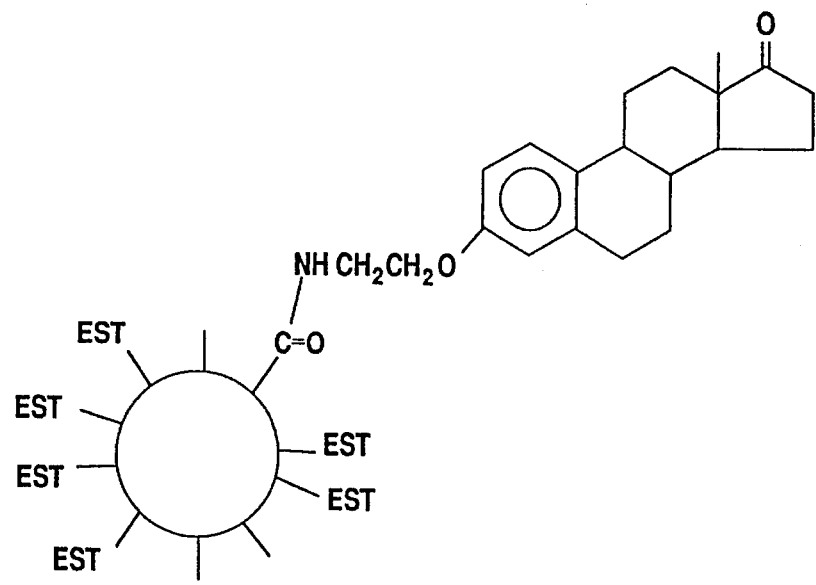

Microcapsules with an average size of 106 μm (range 50–350 μm) and containing cisplatin (40–43%) by weight, were formulated as described in Example 1 from lactic acid polymer and ethylhydroxyethyl cellulose polymer. The capsules, in dry form, were sterilized with ethylene oxide. The microcapsules were suspended in a 1:1 solution of radiographic contrast material. Iohexol (Omnipaque, Nycombed, Norway) and normal saline such that the final concentration was 20 mg/ml. The suspension was administered into the renal artery until stasis of flow was observed fluoroscopically. One kidney was embolized in each of three animals with each of the capsular materials containing CDDP, and one kidney from each of five dogs was occluded with each of the capsular materials without CDDP. Renal and systemic venous blood samples were collected in heparinized tubes at 30-minute intervals for 6 hours after embolization. The plasma was analyzed for CDDP using atomic absorption. Drug release curves were generated from these data. Two such curves are shown in FIGS. 13 and 14. To evaluate renal and hepatotoxicity, systemic venous blood samples were collected before and at 1, 2, 3, 4, and 6 weeks after embolization to determine blood urea nitrogen (BUN), creatinine, and serum glutamic oxaloacetic transaminase (SGPT) levels.

Renal angiography was performed with Omnipaque before and immediately after embolization, at hourly intervals up to 6 hours after embolization, and 1, 2, 4 and 6 weeks later to document the radiographic changes in the occluded kidneys. After 6 weeks, each animal was killed with an overdose of sodium pentobarbital, and a complete necropsy performed. The gross and microscopic findings in each dog were compared.

Both PLA and EHEC capsules without encapsulated drug produced embolic effects in the kidneys. The polymers loaded with cisplatin damaged kidneys significantly more than polymers alone. PLA capsules loaded with cisplatin had a greater effect on tissue than cisplatin-loaded EHEC capsules. EHEC capsules without CDDP showed slightly more degradation than PLA capsules in these studies.

In vitro drug release data were also determined by incubation of the microcapsules in phosphate buffered saline. The data are shown in Table 1 for release of CDDP from CDDP:PLA microcapsules.

TABLE 1

RELEASE RATE OF CDDP FROM CDDP MICROCAPSULES[1] (SIZE 100 μm)

| Incubation Time (min) | % Released |
|---|---|
| 1 | 11.6 |
| 5 | 21.3 |
| 15 | 27.4 |
| 30 | 39.5 |
| 60 | 37.7 |
| 120 | 35.0 |
| 240 | 40.4 |

[1]CDDP:PLA = 1:1

EXAMPLE 5

Biodistribution of 1μ PLA surface Modified Microcapsules

1 μm microcapsules loaded with meglumine diatrizoate were prepared as described in Examples 2 and 3 using PLA and PLA conjugated with phenylalanine (PLA-PHE) as the capsular material. Each preparation was injected intravenously into a rabbit and thereafter monitored by computed tomography for organ uptake. The rabbit receiving PLA-PHE showed a faster liver uptake than the rabbit receiving PLA encapsulated diatrizoate. After 2 hr, the PLA-PHE treated rabbit showed liver uptake and little, if any, contrast in the general circulation while the PLA treated rabbit showed both liver uptake and presence in the general circulation. After 48 and 72 hr, both rabbits showed significant liver uptake. Biodistribution is shown in FIG. 22 which compares tissue distribution of diatrizoate (DZ), $^{131}$I-DZ labeled polylactite (PLA) microcapsules and $^{131}$I-DZ labeled phenylalamine surface modified (PLA-PHE) microcapsules.

Figure 9:
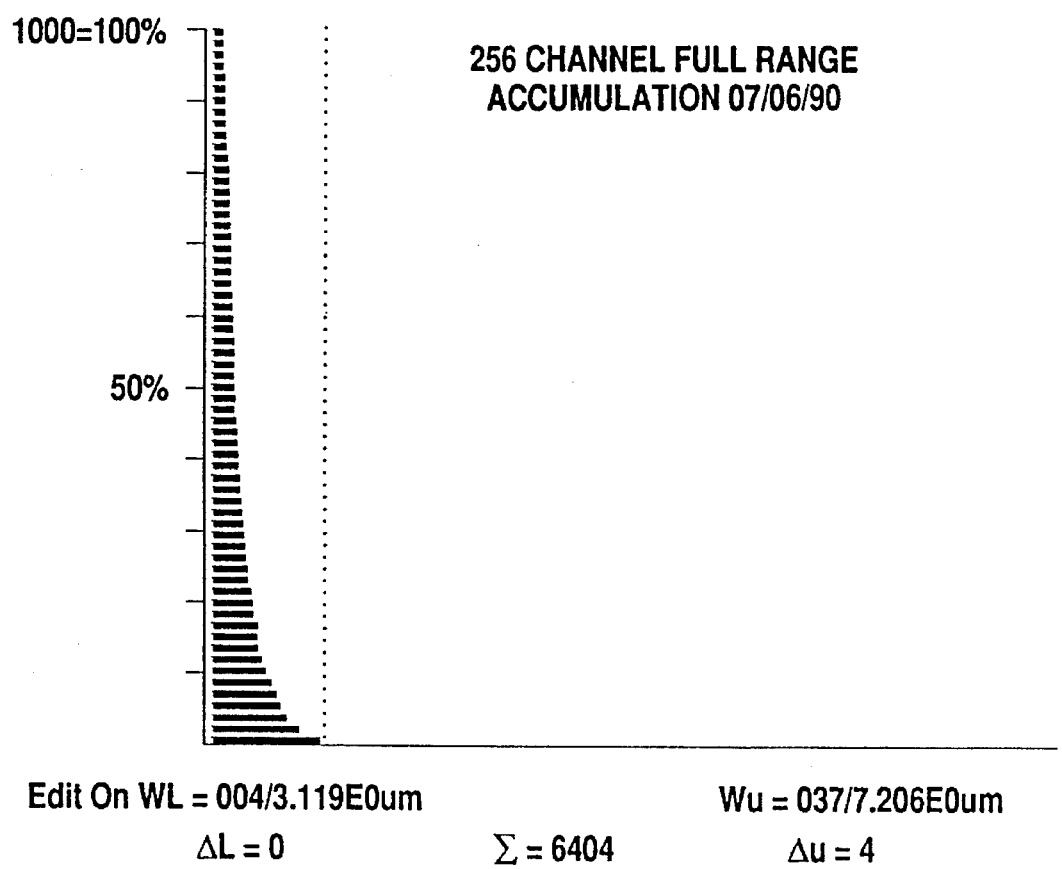
FIG. 9 is a microcapsule size distribution curve prepared from data obtained from Coulter Counter measurements. The mean particle size for the PLA-PHE microcapsules loaded with diatrizoic acid is 3 µm with a range from 2–7 µm.
Figure 10A:
FIG. 10 is a normal mouse hepatocyte culture shown under 40× magnification. All plates were seeded with aliquots from the same cell suspension. 10A shows control (no capsules) hepatocytes; 10B shows hepatocytes incubated for two hours with meglumine diatrizoate-loaded 1 µm poly-(D,L)-lactide capsules.
FIG. 10C shows hepatocytes incubated for two hours with meglumine diatrizoate-loaded 1 µm phenylalanine ester-conjugated poly-(D,L)-lactide capsules.
Figure 10B:
Figure 10C:
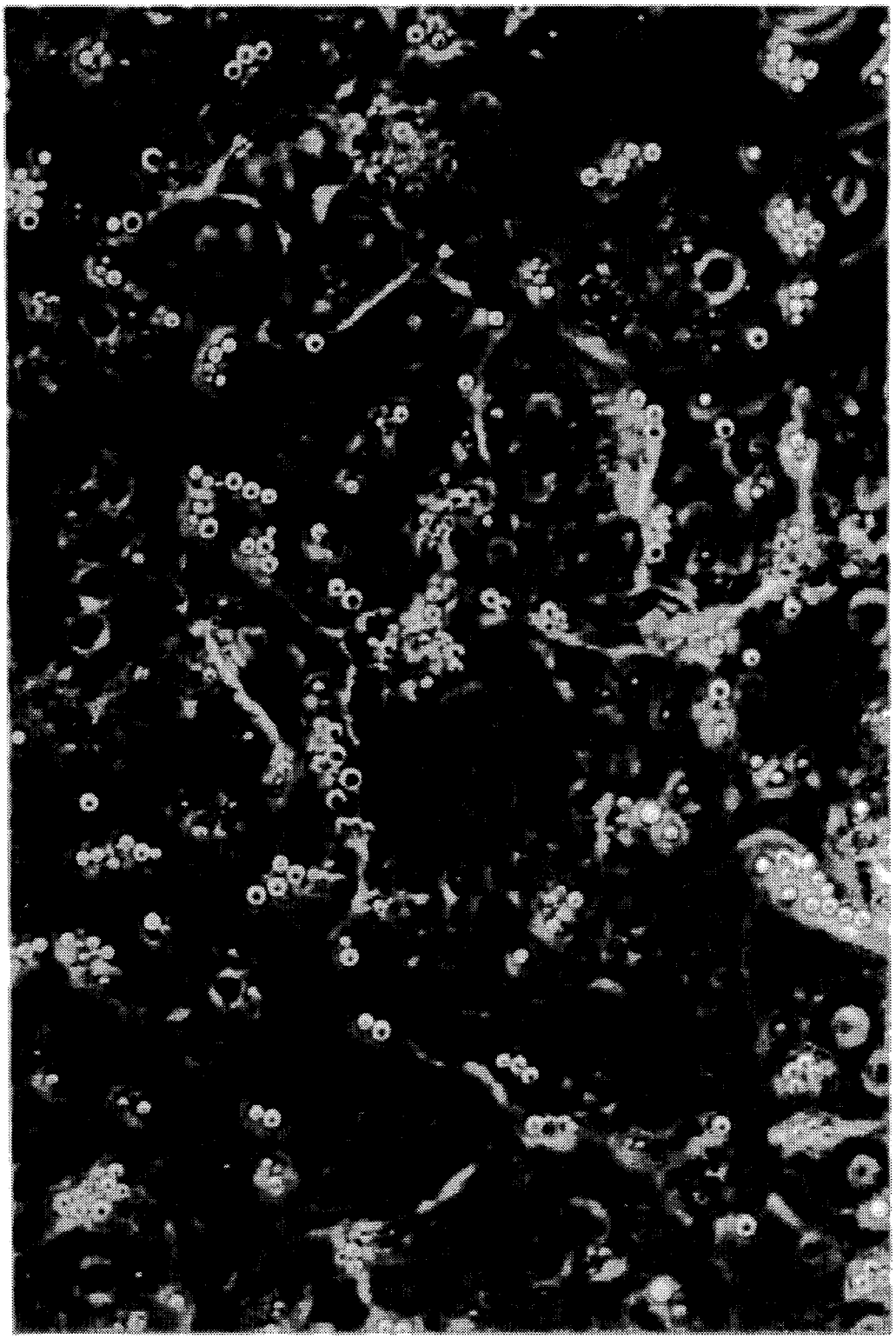
Figure 11A:
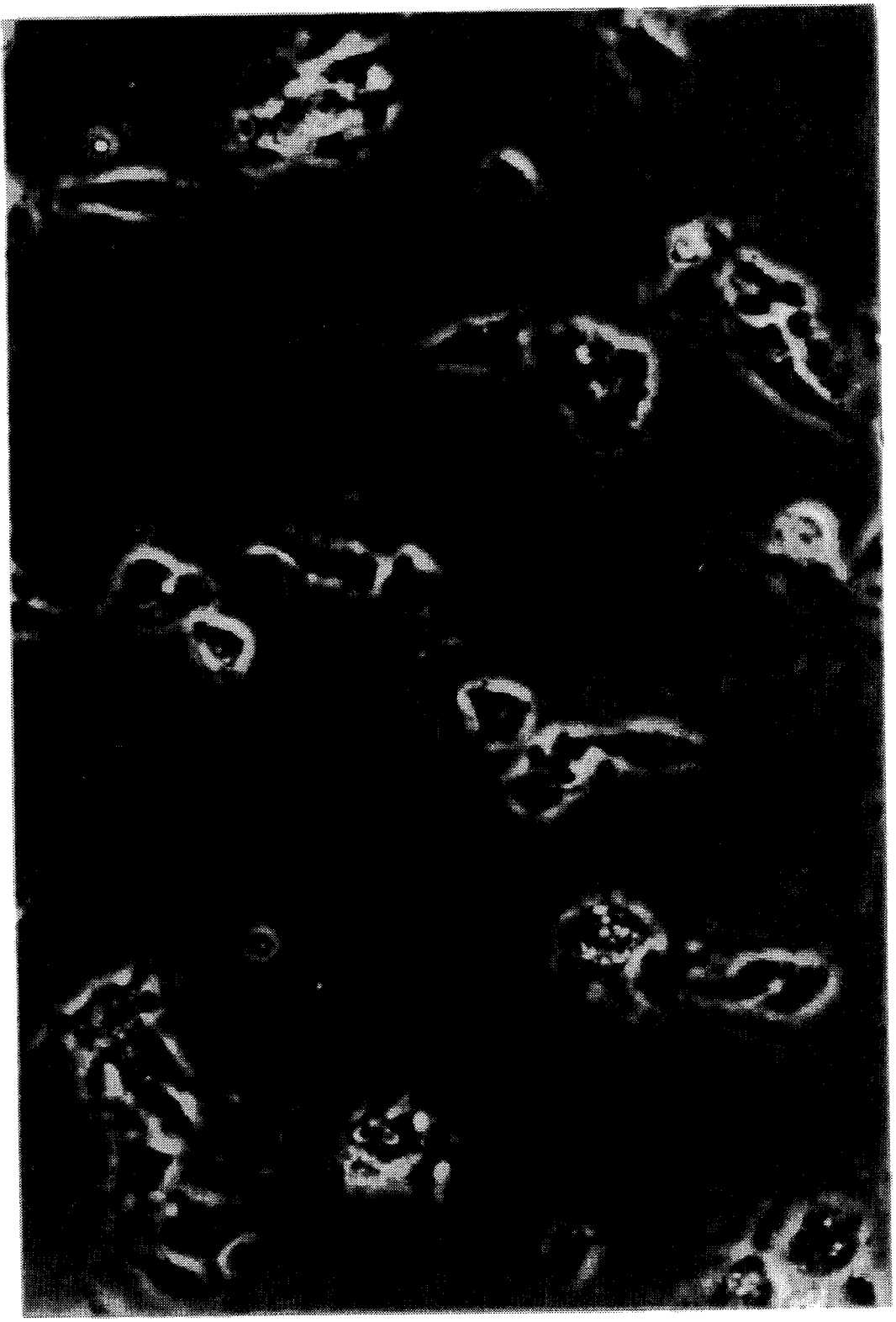
FIG. 11A shows control hepatocytes; 11B shows Kupffer cells after incubation for two hours with 1 µm poly-(D,L)-lactide capsules; 11C shows Kupffer after incubation for two hours with 1 µm phenylalanine ester-conjugated poly-(D,L)-lactide capsules.
Figure 11B:
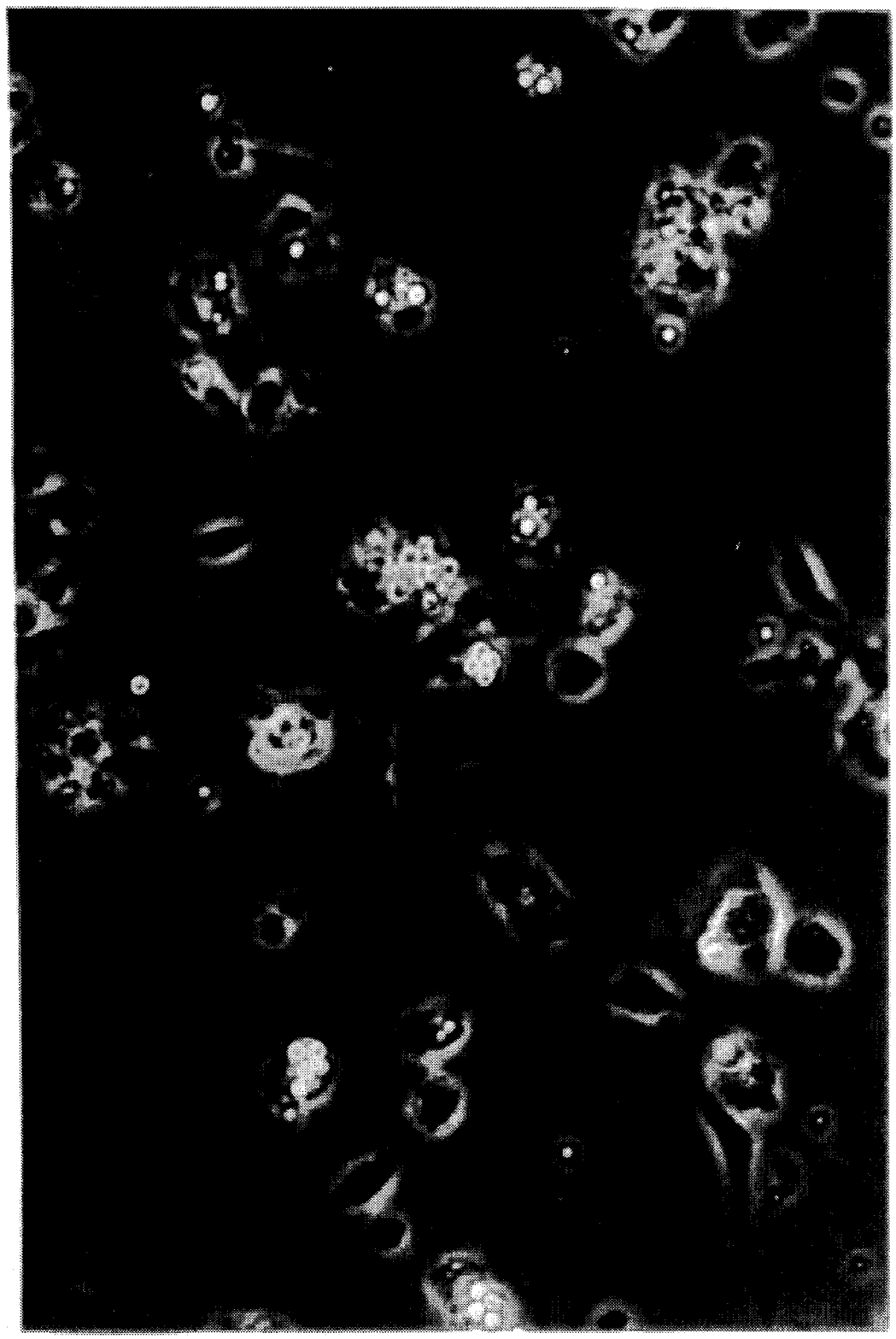
FIG. 11 is a normal mouse Kupffer cell culture shown under 40× magnification. All plates were seeded with aliquots from the same cell suspension.
Figure 11C:
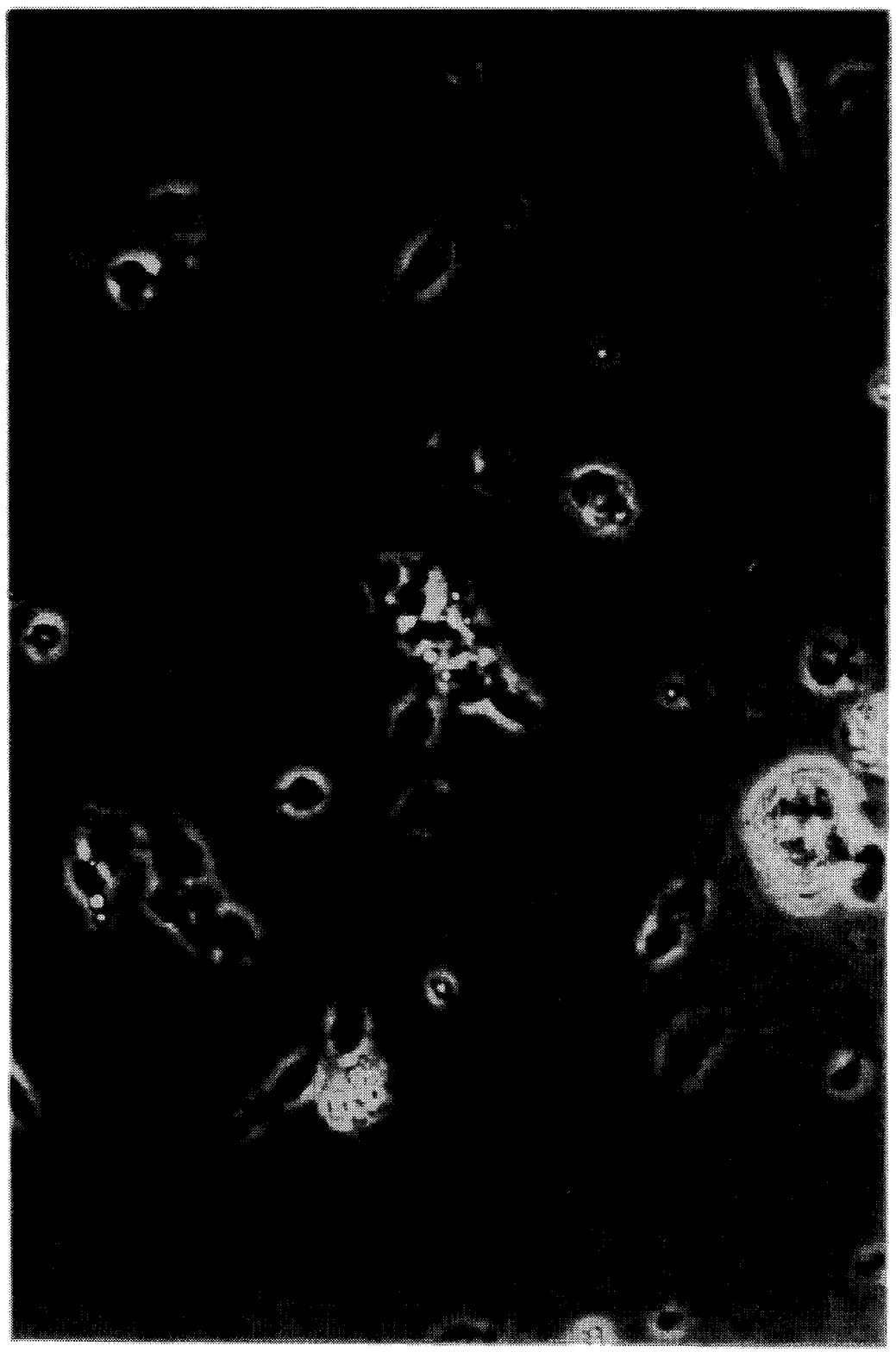
Figures 12A, 12G:
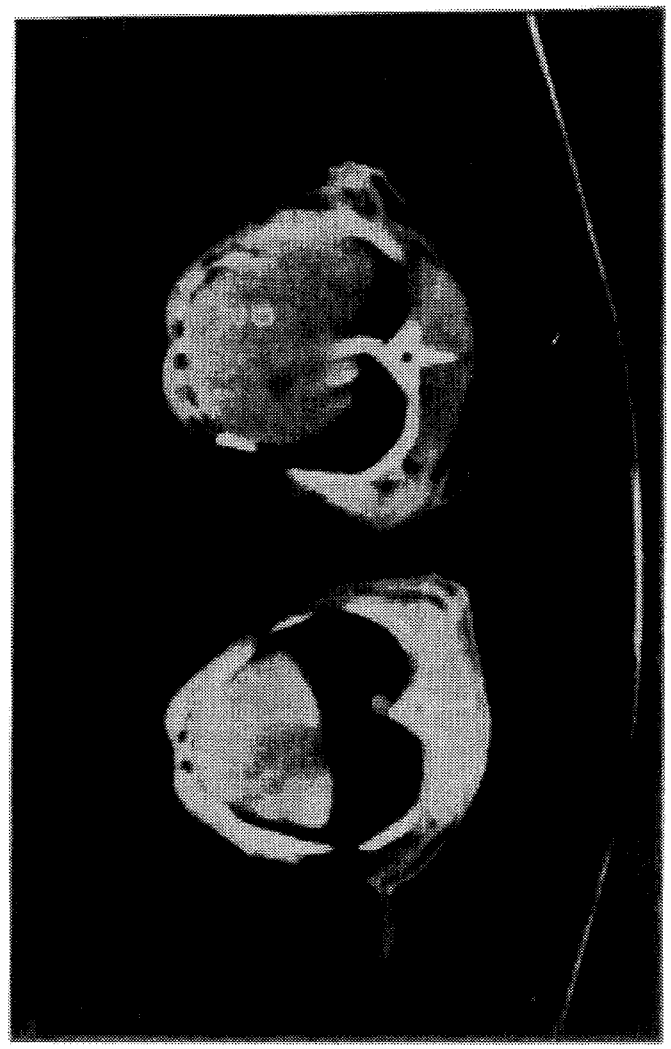
FIG. 12 shows a computerized tomographic images of two rabbits after intravenous injection with microencapsulated meglumine diatrizoate. Panels A–F show distribution of 1 µm poly-(D,L)-lactide capsules loaded with meglumine diatrizoate before (A) and immediately post-injection (B), 1 hr. (C), 2 hr. (D), 57 hr. (E), and 120 hr. (F). Panels G–L show distribution of the 1 µm phenylalanine-conjugated poly-(D,L)-lactide capsules loaded with meglumine diatrizoate before (G) and immediately post-injection (H), 1 hr. (I), 2 hr. (J), 57 hr. (K), and 120 hr. (L).
Figures 12B, 12H:
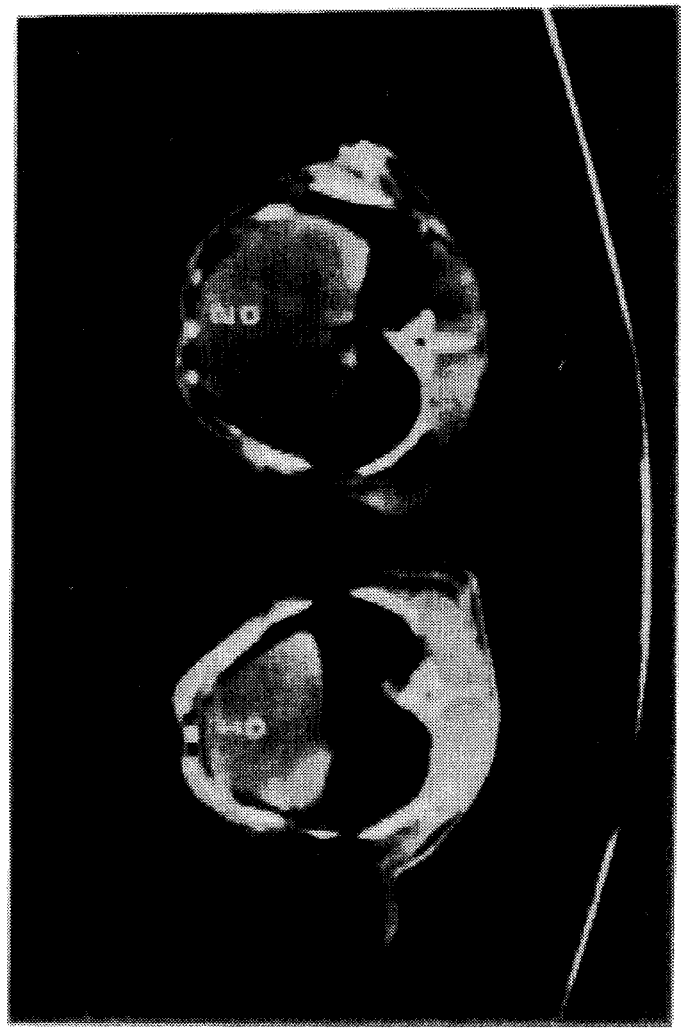
Figures 12C, 12I:
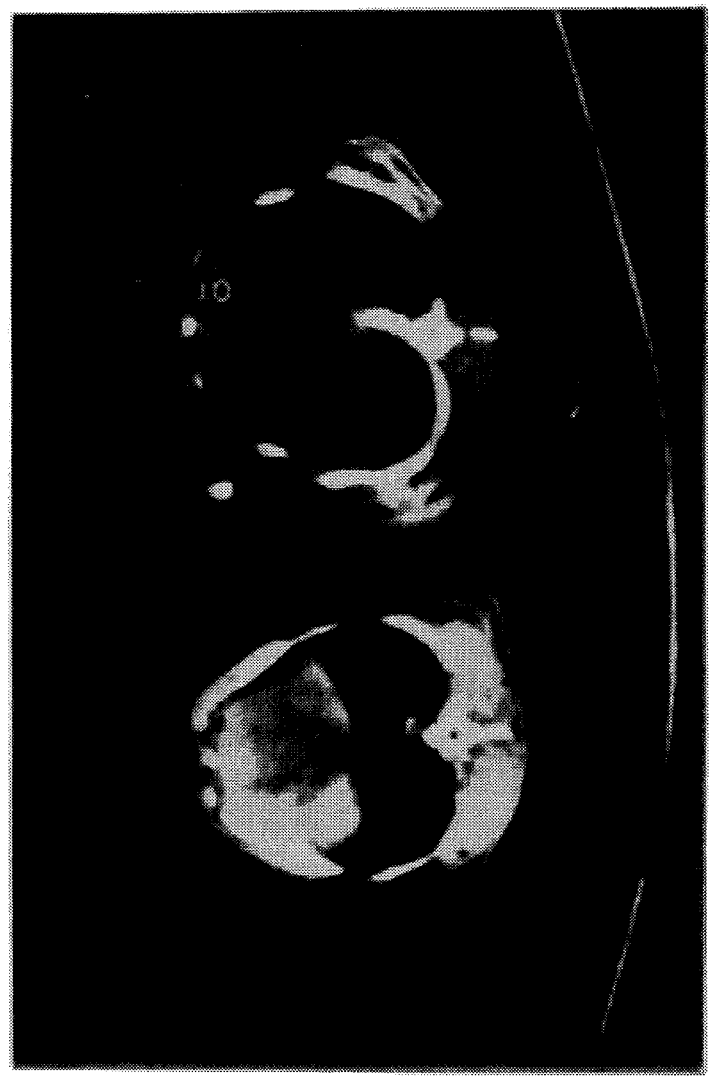
Figures 12D, 12J:
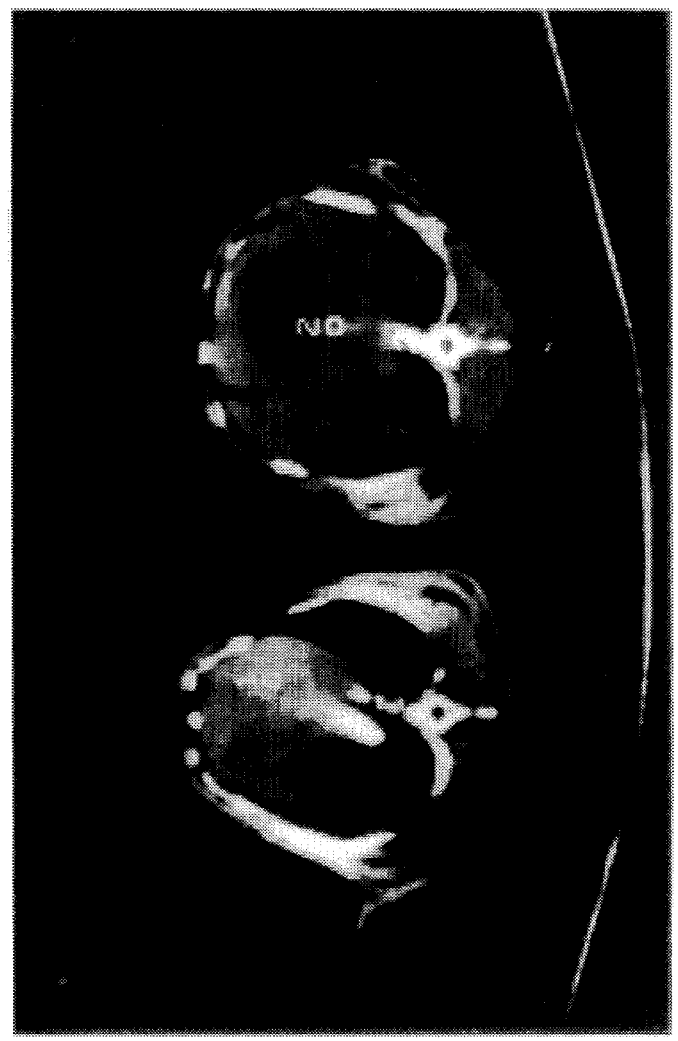
Figures 12E, 12K:
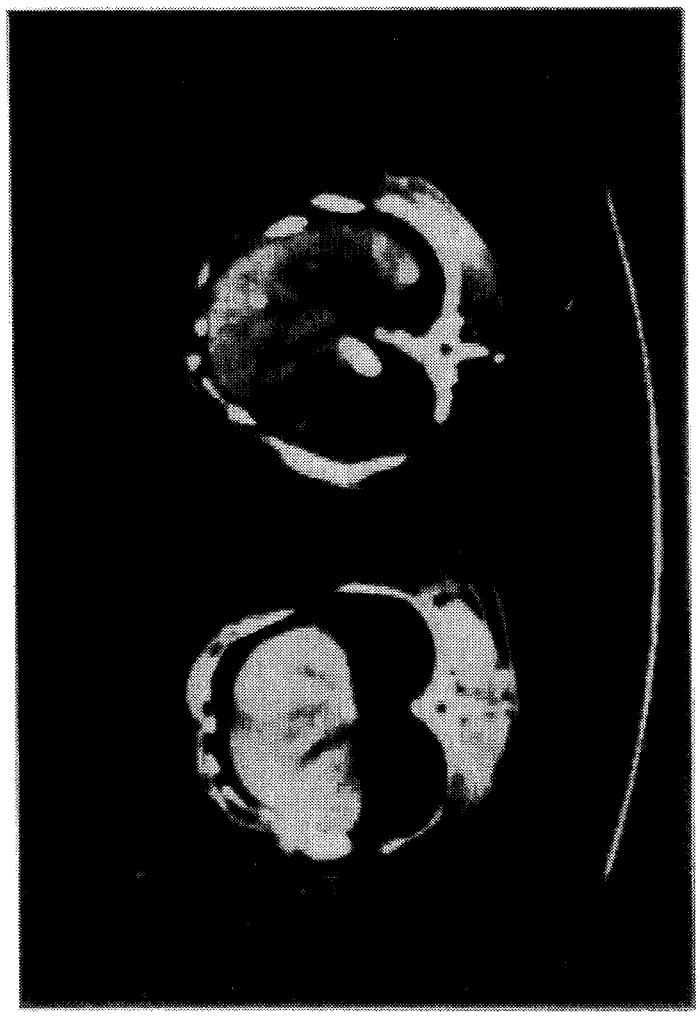
Figures 12F, 12L:
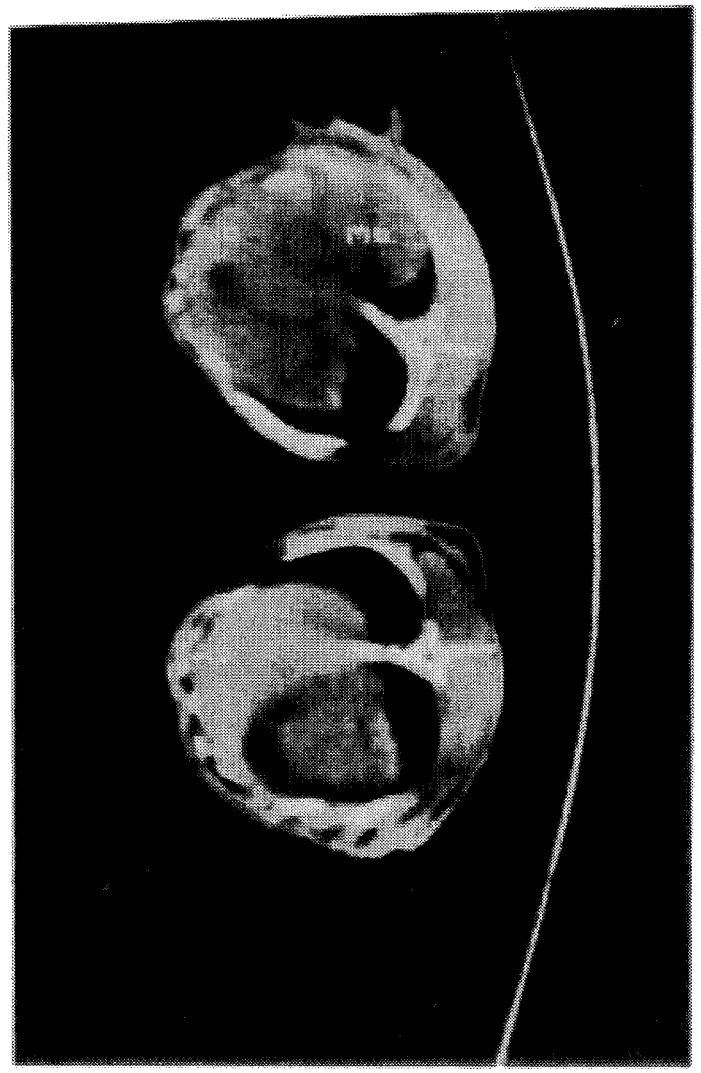

The mean particle size of the PLA-PHE microcapsules loaded with meglumine diatrizoate was determined to be 3 μm, as indicated from a particle size distribution curve obtained using a Coulter Counter, FIG. 9.

In a second series of animal experiments, male Webster mice (25-30 g) were intravenously injected with 1 μC; radiolabeled microspheres, then sacrifieced at 30 min, 1 h, 3 h, 6 h and 24 h. Organs were excised, weighed and counted for radioactivity. The microcapsules exhibited sustained release. Liver uptake was faster in mice injected with labeled pie-modified capsules than in mice receiving labeled unmodified capsules.

EXAMPLE 6

In Vitro Release Rates of 100 μm Microcapsules

Microcapsules were prepared as described in Example 1 using the solvent evaporation method with drug:polymer ratios of 1:1 and 1:3 (w/w) and polyvinyl alcohol as emulsifier. The biodegradable polymers used were PCL, PCLD and polylactic acid (PLA). The cytotoxic compounds Tamoxifen and 5-fluorouracil were dissolved in methylene chloride, then added with the emulsifier to a water solution with stirring at 400 rpm. After 6 hr, the capsules were washed with water and air dried. Capsules of approximately 100 μm were collected from mesh screens. Assays on the encapsulated drugs were performed by dissolving 5 mg of the microcapsules in 5 ml methanol. The solution was centrifuged and 100 μl of the supernatant diluted with 3 ml methanol and analyzed spectrophotometrically at 238 nm. A standard solubility time curve was produced using the same procedure by adding 2 mg of both TX and 5-FU. The drug content was calculated as a percent of total capsule weight. Triplicate determinations were made.

Dissolution studies were performed on the microencapsulated drugs. Capped test tubes were filled with 5 ml of 0.05M phosphate buffered saline pH 7.4 and placed in a water bath shaker set at 100 rpm at 37° C. 5 mg of microcapsules were added to each test tube, and sample solutions of 3 ml were collected at different time intervals after centrifugation. After each determination, the sample solutions were returned to each test tube. The concentrations of the drug released from microcapsules were determined by comparison with the standard drug (2 mg) in the same dissolution solution for the controls and measured spectrophotometrically at 238 nm. Determinations were made in triplicate. A Student's T-test was used to compare the sample after 1 hr of incubation and the corresponding sample at different incubation time intervals (p<0.05 level).

Figure 5:
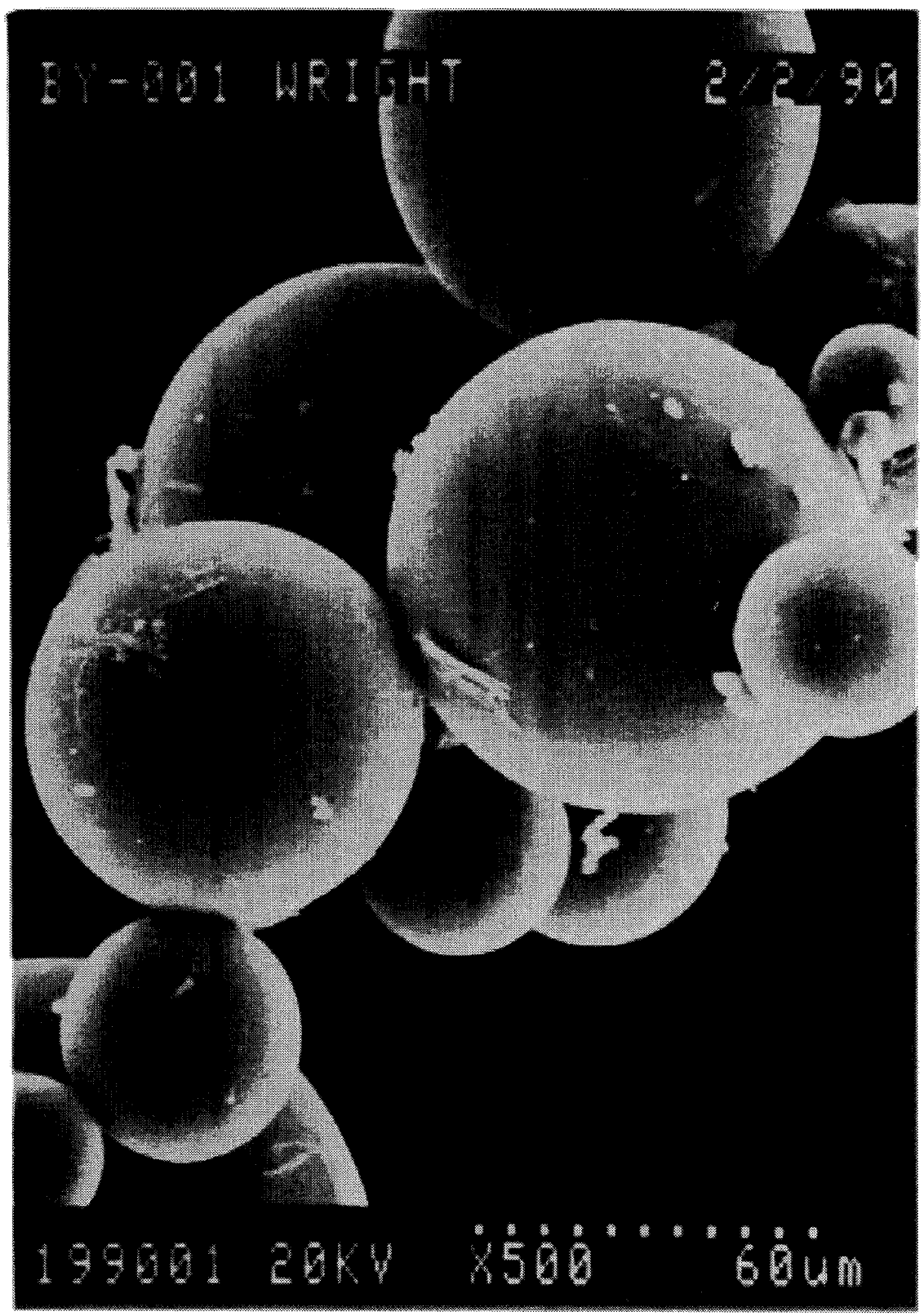
FIG. 5 is a scanning electron micrograph of PLA microcapsules loaded with Tamoxifen with TX:PLA ratios of 1:1.
Figure 6:
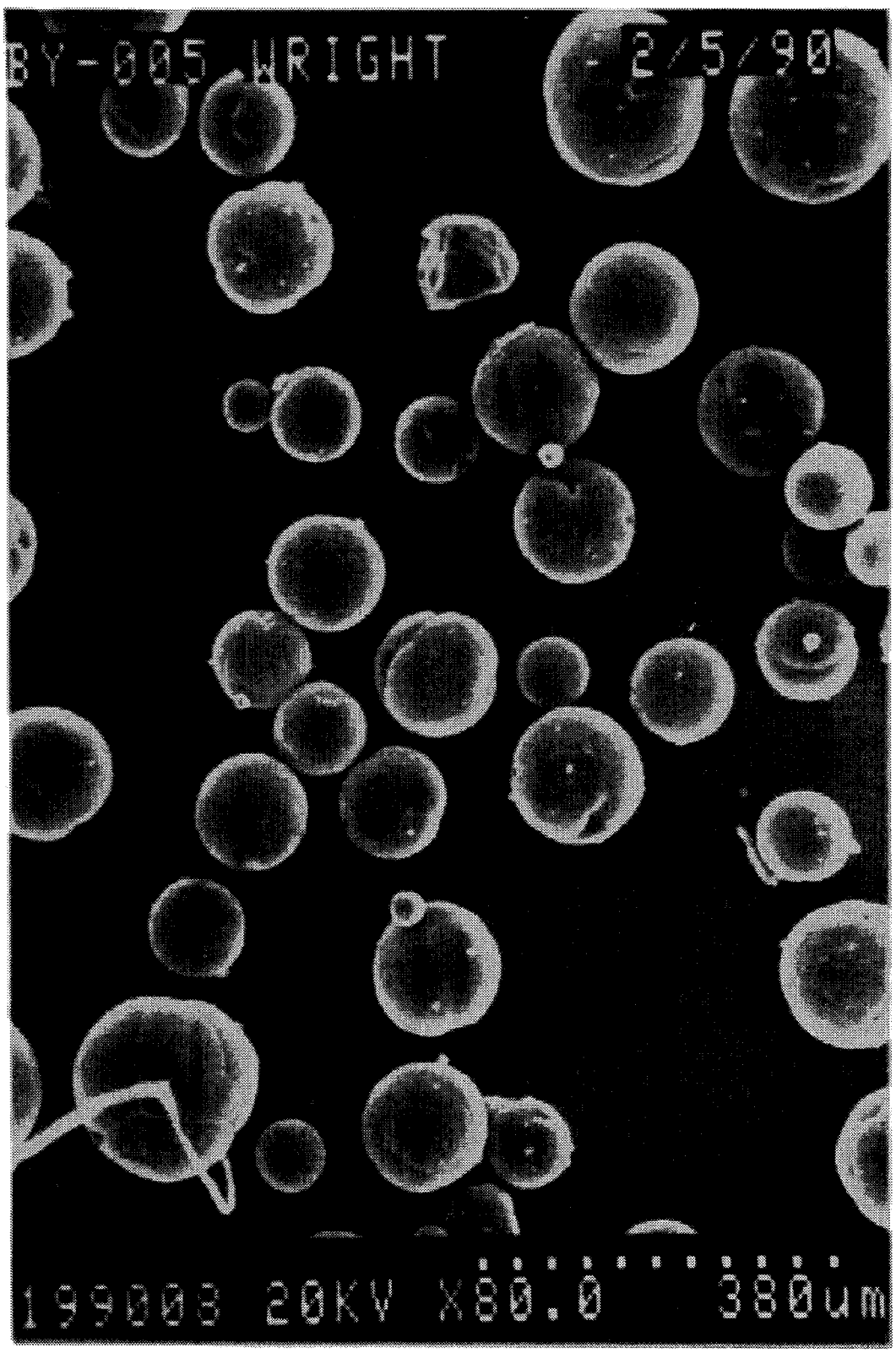
FIG. 6 is a scanning electron micrograph of PCL microcapsules loaded with 5-fluorouracil:PCL ratios of 1:1.

The percent of drug content in the various biodegradable microcapsules is shown in Table 2 below. Scanning electron microscopy showed that all the microcapsules prepared were spherically shaped with smooth outer surfaces (FIGS. 5 and 6).

TABLE 2

% (W/W) DRUG IN MICROCAPSULES

| DRUG | POLYMER | DRUG:POLYMER 1:1 | 1:3 |
|---|---|---|---|
| Tamoxifen | PLA | 30.0 | 22.5 |
| | PCL | 30.7 | 13.0 |
| | PCLD | 36.4 | 14.9 |
| 5-fluorouracil | PLA | 8.8 | 8.5 |
| | PCL | 9.9 | 6.6 |
| | PCLD | 7.6 | 7.6 |

Figure 2:
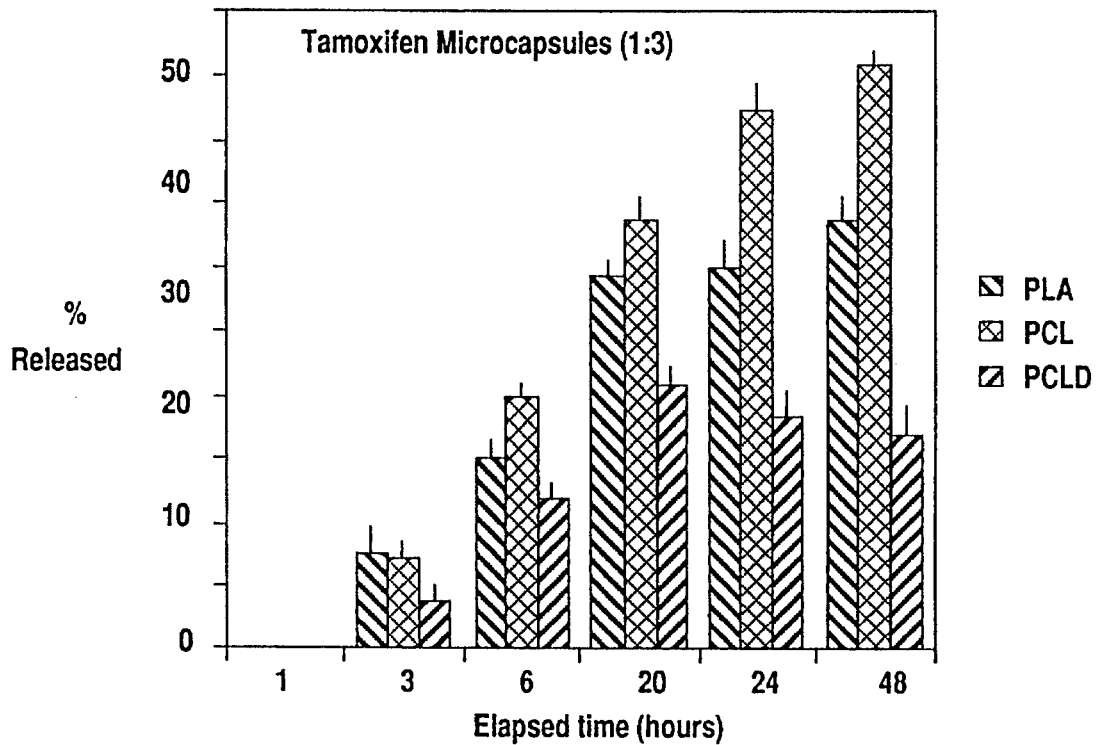
FIG. 2 shows the in vitro release rate profile of Tamoxifen from Tamoxifen microcapsules with Tamoxifen:polymer ratios of 1:3. A statistically significant difference from the corresponding sample after 1 hr of incubation (p<0.05, Student T-test) was determined. Each bar represents the mean±standard deviation of three samples.
Figure 3:
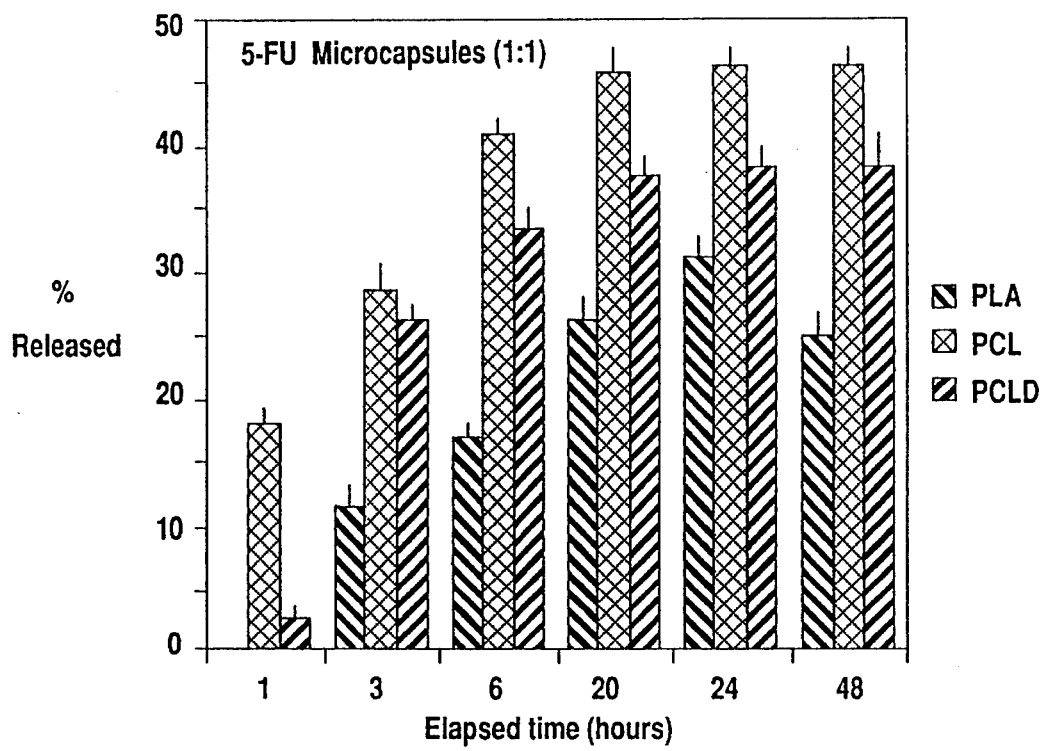
FIG. 3 shows the in vitro release rate profile of 5-fluorouracil from 5-fluorouracil microcapsules with 5-fluorouracil:polymer ratios of 1:1. A statistically significant difference from the corresponding sample after 1 hr of incubation time (p<0.05, Student T-test) was determined. Each bar represents the mean±standard deviation of three samples.
Figure 4:
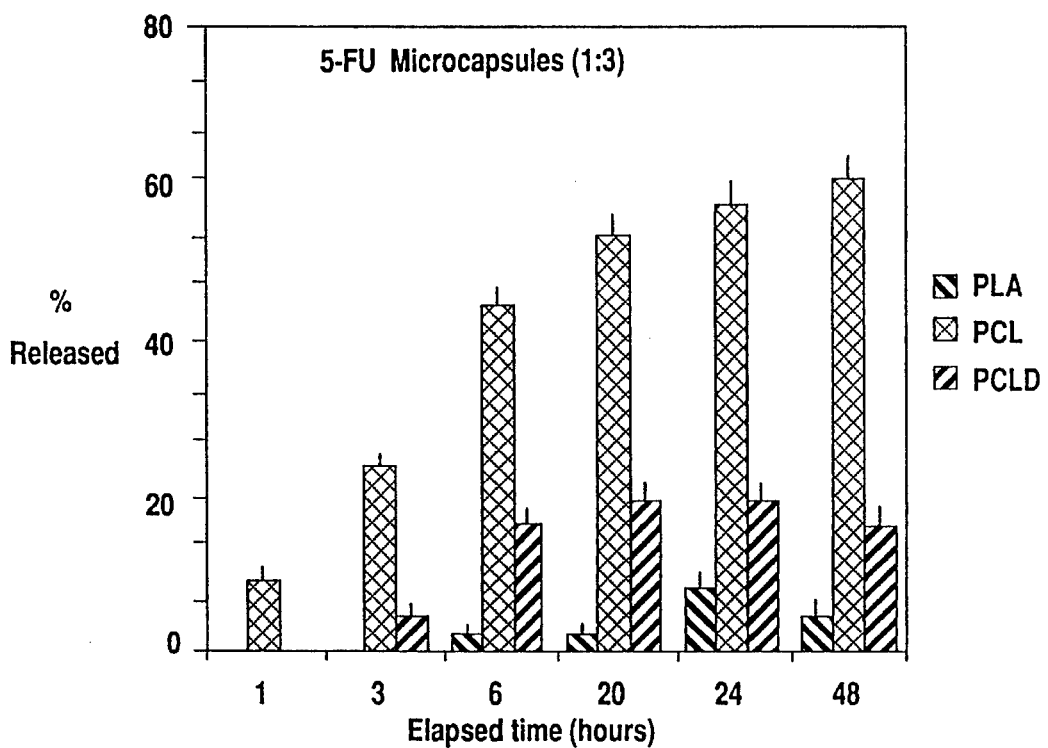
FIG. 4 shows the in vitro release rate profile of 5-fluorouracil microcapsules with 5-fluorouracil ratios of 1:3. A statistically significant difference from the corresponding sample after 1 hr of incubation (p<0.05, Student T-test) was determined. Each bar represents the mean±standard deviation of three samples.

Release rate of TX and 5-FU is shown in FIGS. 1 and 2. The release rate of TX (1:1 ratio) at 48 hr incubation time decreased in the order: PLA>PCL>PCLD; however, the release rate of 5-FU (1:1 and 1:3 ratios) at 48 hr incubation showed PCL>PCLD>PLA. This study indicates that different polymers alter drug release rate.

EXAMPLE 7

Preparation of PHPG Microspheres

Poly(benzyl L-glutamate)(PBLG, Sigman) microspheres were prepared by a solvent evaporation method according to Example 1. Polybenzyl-L-glutamate (PBLG, 0.7 g) and unlabeled ethyliopanoate (0.3 g) were dissolved in methylene chloride (30 ml). To this mixture [$^{131}$I]ethyliopanoate (320 µCi) was added. The organic phase was emulsified in a water solution (200 ml) containing polyvinyl alcohol (1% w/v). The mixture was stirred at 2000 rpm for 25 hours to ensure complete evaporation of the solvent. The suspension was then centrifuged (12,000 rpm) for 10 minutes. The microcapsules were separated, washed with water to remove any excess polyvinyl alcohol and centrifuged again. The resulting microcapsules were filtered through nylon cloth (5-µm mesh). The final concentration was 154 µCi in 18 ml of water. In a typical run, particles had a mean diameter of 2.0 µm and over 95% of particles were less than 5 µm.

PBLG microspheres were converted to PHPG hydrogel microspheres by treating PBLG with aminopropyl alcohol containing 3% of diaminohexane as a crosslinker at 70° C. for 2,3 or 5 hrs. To determine the extent of conversion, PHPG microspheres were completely hydrolyzed and the unsubstituted benzyl groups analyzed by HPLC.

FIG. 21 illustrates the conversion of poly(benzyl L-glutamate) to poly(hydroxypropyl L-glutamine). A schematic representation of the microspheres formed from the polymer is also shown.

Radiolabeling of Microsphere

Microspheres were labeled with covalently bound $^{131}$I prepared by treating PBLG microspheres with aminopropyl alcohol in the presence of tyramine (1% w/w) followed by Iodogen labeling (Wallace, et al., 1988). Radiochemical yield:65% with purity >95%.

In Vitro Stability Assay $^{131}$I labeled PHPG particles (20 µCi/mL) were incubated in 50% serum at 37° C. At various time intervals, aliquots of serum were removed and centrifuged. The radioactivity of supernatant was measured with a γ-counter.

Organ Distribution of Microspheres

Female Sprague-Dawley rats (140–160 g) were anesthetized with ketamine (10 mg, i.p.) and radiolabeled microspheres were given i.v. (0.4 mL). The dose corresponded to 12 mg dry microspheres with total activity of 6±2 µCi. The animals were sacrificed at 20 min, 3, 6, 24, 48 and 96 hrs. The organs were excised, weighed and counted for radioactivity.

Electron Microscopy Studies

Liver tissue samples were examined by TEM. 30 min after administration of microspheres, liver was perfused with 2% glutaraldehyde in 0.2M sodium cacodylate buffer through the portal vein. Tissue samples were processed and stained using standard TEM methods. SEM of air dried microspheres were examined in a Hitachi model S520 electron microscope.

PHPG microspheres were prepared directly from PBLG microspheres by aminolysis. This approach made it possible to prepare a series of PHPB microspheres with different surface characteristics. The resulting microspheres became increasingly hydrophilic with longer reaction times. Swelling ratio increased from 3% (PBLG microspheres) to 36% (PHPG microspheres) after 4 hrs treatment with aminopropyl alcohol. The hydrophilicity of PHPG microspheres was also evidenced by SEM which showed that the microspheres tend to become flat after drying in air.

Only 1% of radioactivity dissociated from PHPG microspheres after incubation in 50% serum for 2 hrs. 96% of radioactivity was found bound to PHPG microspheres even after two days. FIG. 18 shows the deposition of three preparations of PHPG microspheres in liver, blood and spleen 20 minutes post-administration. With the increased hydrophilicity of the microspheres, there was a substantial decreased uptake in liver; the concentration of microspheres circulating in the blood was increased. This indicated decreased uptake of microspheres in liver Kupffer cells achieved by modification of PHPG microspheres. Electron microscopic studies revealed that PBLG microspheres were taken up by Kupffer cells. On the other hand, no PHPG microspheres could be identified in the Kupffer cells of rats.

EXAMPLE 8

The following example illustrates modification of the phenolic group of estrone to enable coupling with polybenzyl-L-glutamate. The product illustrates a "spacer" between the estrone 3-position functionality and the conjugating amide bond.

Preparation of 3-Aminoethyl Estrone

Estrone (5.0 g, 18.5 mmole) was dissolved in 80 mL of anhydrous DMF. Sodium hydride (4.4 g, 185 mmole) was slowly added to the solution to generate reactive phenoxide in situ. Care was taken to avoid rapid evolution of hydrogen gas. 4.3 g (55 mmole) chloroethylamine was added to the solution and the mixture was allowed to react at 60° C. for 4 hrs. The product was precipitated with a large volume of water and the precipitate collected. For purification, the crude solid was dissolved in methylene chloride, and washed with water. Evaporation of methylene chloride yielded 3-aminoethyl estrone which after washing with ethyl ether gave 3.0 g (52%) of product m.p. 140° C. (decomp.), 3-aminoethyl estrone hydrochloride, m.p. 180° C. (decomp.), $^1$HNMR (ppm): δ3.01 (2,t,CH$_2$$\underline{CH_2}$NH$_2$), 2.78 (2,t,$\underline{CH_2}$,CH$_2$NH$_2$), 4.00 (2,t,COCH$_2$).

Coupling of 3-Aminoethyl Estrone to Poly(benzyl L-glutamate) (PBLG)

The reaction below was conducted in p-dioxane as solvent. The reaction may also be conducted in dimethyl sulfoxide or dimethyl formamide with comparable success; however these solvents are not so readily removed and are therefore less preferable.

3-Aminoethyl estrone (1.25 g, 4 mmole) was added to a 7 mL dioxane solution of PBLG (0.88 g, 4 mmole). The mixture was allowed to react at 60° C. for 2 days. The conjugate formed was collected by precipitating the dioxane solution with water, followed by filtration. For purification, the solid was dissolved in methylene chloride. Insoluble impurities were removed by filtration. The methylene chloride solution was washed with cold aqueous 0.2N hydrochloric acid solution (×2), water, and saturated NaCl until neutral. Evaporation of methylene chloride yielded 0.4 g product. Elemental analysis for the conjugate, calculated, C: 70.73; H: 7.60; N: 6.60; found, C: 66.70; H: 6.45; N: 6.00. Degree of substitution was calculated to be 12% based on elemental analysis data. $^1$HNMR (ppm): $\delta$3.70 (2,t,CH$_2$CH$_2$NHCO), 2.86 (2,t,CH$_2$CH$_2$NHCO), 4.04 (2,t,COCH$_2$).

Estrone-conjugated poly-benzyl-L-glutamate was dissolved in p-dioxane and used to prepare 1 μm microcapsules by the method of Example 2.

EXAMPLE 9

This example illustrates determination of binding affinity constants for estradiol in pig uterus.

In Vitro Estrogen Receptor Assay

Figure 16A:
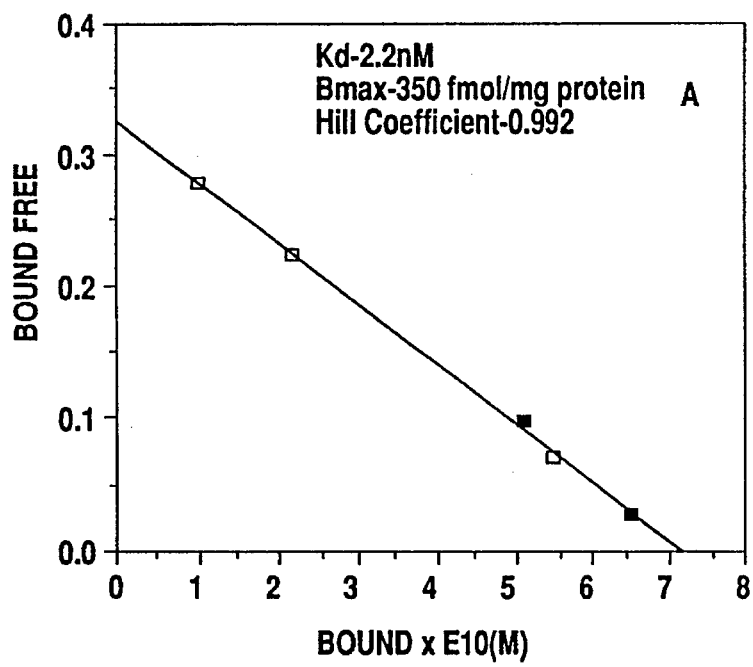
FIG. 16A is Scatchard analysis; 16B shows the saturation curve for estrogen receptor binding assay in pig uteri.
Figure 16B:
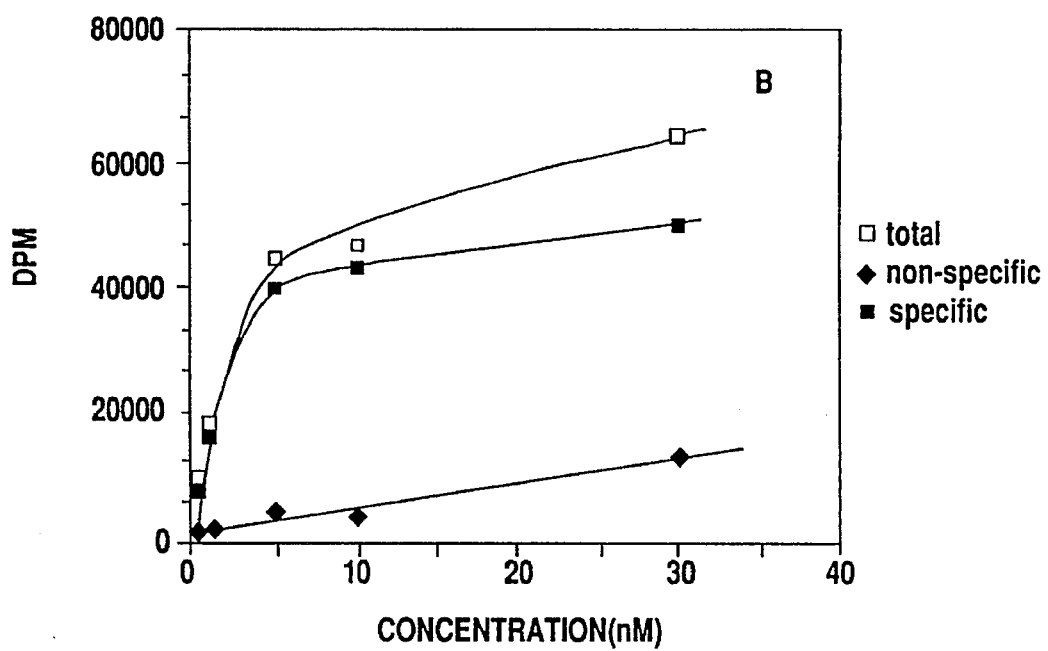
FIG. 16 shows an estrogen receptor assay.

Affinity for binding the estrogen receptor was determined. 30 g uteri obtained from domestic swine (30 kg) were homogenized in 80 ml of 10 mM Tris buffer, pH 7.4, containing 1.5 mM EDTA and 3 mM sodium azide. The homogenate was centrifuged at 1,000×g for 1 hr at 4° C. Uteri cytosol was then pretreated with dextran-coated charcoal. To investigate the nature of estradiol interaction with the estrogen receptor site, a saturation curve was obtained from [$^3$H]estradiol ($10^{-5}$M to $10^{-10}$M) in the presence or absence of excess estradiol ($10^{-5}$M)(FIG. 16). Uteri cytosol was incubated at 4° C. for 2 hr with [$^3$H]estradiol (5 nM/tube) and competitor (ranging from $10^{-3}$ M to $10^{-8}$M) or with estradiol ($10^{-5}$M)(non-specific). The concentration of test compounds that decreased specific radioligand binding by 50% (IC$_{50}$) was measured. Protein concentrations were determined according to the method of Lowry et al. (1956).

Scatchard analysis indicated a single class of binding sites with a mean binding affinity constant kd of 2.2 nM (n=9) and a mean receptor density (B max) of 350 fmol/mg protein, FIG. 16. The protein concentration used was 1 mg/ml cytosol. Hill analysis (0.992) indicated that estradiol had competitive reversible binding. The IC$_{50}$ of estrone conjugates to polybenzyl-L-glutamate was $5\times10^{-7}$M which is ten-fold lower than the binding affinity for estrone ($5\times10^{-8}$M), Table 3.

TABLE 3

Comparison of EST-PG and Estrone on Estrogen Receptor Binding in Pig Uterus

|  | IC$_{50}$ (M) | Equiv. (Wt) |
|---|---|---|
| Estrone | $5 \times 10^{-8}$ | 0.14 ng |
| EST-PG[a] | $5 \times 10^{-7}$ | 500 ng |

[a]EST-PG: Estrone with spacer (ethanolamine) conjugates to polybenzylglutamate (MW 58,000)
[b]Based upon 12.0% of conjugation between estrone and polymer, determined by UV at 282 nm and elemental analysis.

EXAMPLE 10

This example provides data comparing percent tissue uptake of estrone loaded polybenzyl-L-glutamate microcapsules containing $^{131}$I-iopanoate with microcapsules containing $^{131}$I-iopanoate but lacking estrone. Of significance is the greater uptake of the estrone loaded microcapsules by the uterus whereas there is less relative uptake by microcapsules containing only the labeling agent.

In Vivo Tissue Uptake

Estrone conjugated poly-benzyl-L-glutamate microcapsules loaded with $^{131}$I-labeled ethyliopanoate were injected into rats (three per group) via the tail-vein (5.7 μCi in 0.3 ml water). Control groups were given only the $^{131}$I-labeled iopanoic acid. Rats were sacrificed at 1, 3, 6 and 24 hours post injection. The percent of injected dose per organ or per tissue weight was determined by a COBRA Auto-gamma counter (Packard, Meridien, Conn.). Results are shown in Tables 4 and 5.

TABLE 4

Tissue Distribution of $^{131}$I-IOPA Loaded Estrone Poly(benzyl L-glutamate) Conjugate Microspheres after I.V. Injection Into Rat (n = 3)[1,2].

| Organ | 1 hr mean (s.d.) | 3 hr mean (s.d.) | 6 hr mean (s.d) | 24 hr mean (s.d.) |
|---|---|---|---|---|
| blood | 1.01 (0.12) | 0.72 (0.08) | 0.46 (0.01) | 0.09 (0.03) |
| lung | 1.05 (0.15) | 0.53 (0.03) | 0.34 (0.02) | 0.07 (0.03) |
| liver | 1.34 (0.18) | 0.75 (0.09) | 0.56 (0.03) | 0.17 (0.02) |
| kidney | 0.52 (0.01) | 0.62 (0.05) | 0.26 (0.01) | 0.06 (0.02) |
| uterus | 0.70 (0.12) | 0.62 (0.01) | 0.39 (0.05) | 0.06 (0.01) |
| muscle | 0.20 (0.01) | 0.12 (0.01) | 0.09 (0.01) | 0.01 (0.01) |
| fat | 0.37 (0.01) | 0.20 (0.02) | 0.14 (0.01) | 0.03 (0.01) |

[1]IOPA = ethyl iopanoic acid.
[2]Data shown represents percent of injected dose per gram tissue.

TABLE 5

Tissue Distribution of $^{131}$I-IOPA Loaded Poly(benzyl L-glutamate) Conjugate Microspheres after Intravenous Injection Into Rat (n = 3)[1,2].

| Organ | 1 hr mean (s.d.) | 3 hr mean (s.d.) | 6 hr mean (s.d) | 24 hr mean (s.d.) |
|---|---|---|---|---|
| blood | 1.53 (0.71) | 1.46 (0.21) | 1.30 (0.26) | 0.29 (0.16) |
| lung | 1.86 (0.40) | 1.06 (0.16) | 1.02 (0.19) | 0.28 (0.03) |
| liver | 1.80 (0.78) | 1.20 (0.15) | 1.16 (0.14) | 0.54 (0.16) |
| kidney | 0.74 (0.28) | 0.58 (0.09) | 0.58 (0.05) | 0.24 (0.08) |
| uterus | 0.85 (0.29) | 0.76 (0.02) | 0.73 (0.10) | 0.14 (0.01) |
| muscle | 0.32 (0.16) | 0.24 (0.02) | 0.21 (0.03) | 0.05 (0.01) |
| fat | 0.83 (0.29) | 0.58 (0.23) | 0.36 (0.11) | 0.07 (0.04) |

[1]IOPA = ethyl iopanoic acid.
[2]Data shown represent percentage of injected dose per gram tissue.

Relative Tissue Uptake of Modified Microcapsules

Table 6 shows the distribution of $^{131}$I-labeled ethyliopanoate in rats in terms of uterus to muscle ratio. After 3 hr, the targeting of the estrone-conjugated labeled microcapsules was significantly greater than targeting by the labeled microcapsules or by labeled ethyliopanoate.

TABLE 6

Distribution of $^{131}$I-Labeled Ethyliopanoate in Rats.
UTERUS TO MUSCLE RATIO

| Time (hrs) | 1 | 3 | 6 | 24 |
|---|---|---|---|---|
| IOPA[1] | 2.92 ± 0.464 | 3.60 ± 0.346 | 3.47 ± 0.122 | n.d.[3] |
| PBLG[1] | 2.84 ± 0.447 | 3.23 ± 0.300 | 3.48 ± 0.369 | 2.76 ± 0.214 |
| PE[1] | 3.50 ± 0.433 | 5.16 ± 0.592[2] | 4.75 ± 0.354[2] | 4.25 ± 1.061[2] |

[1]IOPA: ethyliopanoate, PBLG: polybenzylglutamate microcapsules loaded with IOPA, PE: microcapsules of estrone and PELG conjugate. Each rate received 5 uCi of radiotracer in saline (0.25 ml).
[2]Significant difference (p < 0.05) between PE and the corresponding groups by student T-test.

[3]n.d.: not detectable.

EXAMPLE 11

Preparation of PEG-IOPA Conjugate

Novel hydrophilic microcapsules may be prepared utilizing hydrophilic polymers for formation of microcapsules. In the following Example, polyethylene glycol (PEG) is covalently attached to a labeling agent, iopanoic acid. It is contemplated that this material may be readily formulated into microcapsules according to Example 1.

Into 6 mL methylene chloride solution containing 1.45 g poly(ethylene glycol) (PEG, MW 1450, 1.0 mmol) was added 1.43 g iopanoic acid (IOPA, 2.5 mmol), 454 mg dicyclohexylcarbodiimide (DCC, 2.2 mmol) and 24 mg dimethylaminopyride (0.24 mmol). The reaction mixture was stirred overnight at room temperature. After filtration to remove dicyclohexylurea (DCU) precipitate the solution was evaporated to dryness. The residual was then washed with dry ether three times to yield a hygroscopic solid. Yield 1.15 g(45%). Iodine content 20–30% (w/w). Using the microcapsule preparation according to Example 1, the product is then formulated as particles (<5 μm) which are suitable for iv injection.

Figure 23:
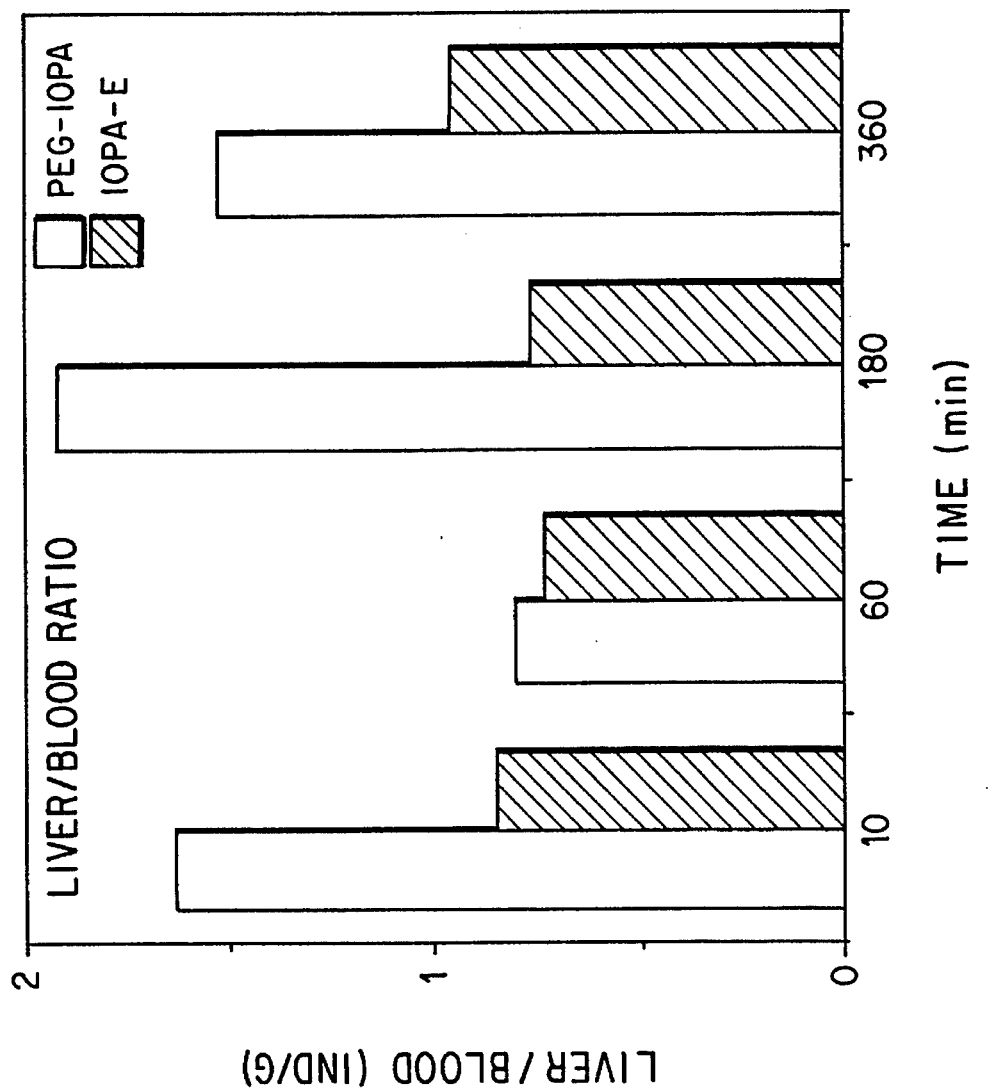
FIG. 23 compares liver/blood uptake ratio over a period of approximately 6 hr for polyethylene glycol conjugated iopanoic acid (PEG-IOPA) and iopanoic acid (IOPA-E).

In vivo biodistribution of $^{131}$I-IOPA attached to polyethylene glycol (PEG) is shown in Tables 7 and 8. The ratio of liver to blood uptake of $^{131}$I-IOPA is altered by the presence of PEG which is hydrophilic. The changes in liver/blood uptake ratio conferred by conjugation of $^{131}$I-IOPA to PEG are illustrated in FIG. 23.

TABLE 7

Organ Distribution of $^{131}$I PEG-IOPA Solution
After Intravenous Injection to Rats (n = 3)

| Organ | 10 min | 1 hr | 3 hr | 6 hr |
|---|---|---|---|---|
| blood | 1.67 (0.05) | 1.62 (0.19) | 0.54 (0.13) | 0.39 (0.18) |
| lung | 0.65 (0.08) | 0.38 (0.14) | 0.06 (0.02) | <0.01 |
| spleen | 0.64 (0.04) | 0.24 (0.04) | 0.03 (0.01) | <0.01 |
| liver | 2.74 (0.50) | 1.28 (0.12) | 1.00 (0.02) | 0.55 (0.09) |
| kidney | 1.78 (0.13) | 0.83 (0.09) | 0.49 (0.07) | 0.27 (0.06) |
| muscle | <0.01 | | | |
| liver/blood | 1.64 (0.34) | 0.80 (0.10) | 1.92 (0.47) | 1.53 (0.43) |

TABLE 8

Organ Distribution of $^{131}$I PEG-IOPA Suspension
After Intravenous Injection to Rats (n = 3)

| Organ | 20 min | 1 hr | 3 hr | 6 hr |
|---|---|---|---|---|
| blood | 3.18 (0.38) | 2.01 (0.06) | 2.15 (0.48) | 1.36 (0.06) |
| lung | 1.73 (0.14) | 1.01 (0.11) | 0.93 (0.25) | 0.98 (0.13) |
| liver | 2.72 (0.95) | 1.52 (0.05) | 1.57 (0.33) | 1.29 (0.08) |
| kidney | 1.72 (0.07) | 0.99 (0.04) | 1.09 (0.18) | 0.88 (0.11) |
| muscle | 0.89 (0.14) | 0.44 (0.08) | 0.40 (0.06) | 0.26 (0.02) |
| liver/blood | 0.85 (0.24) | 0.73 (0.03) | 0.76 (0.02) | 0.95 (0.10) |

The present invention has been described in terms of particular embodiments found by the inventors to comprise preferred modes of practice of the invention. It will be appreciated by those of skill in the art that in light of the present disclosure numerous modifications and changes can be made in the particular embodiments exemplified without departing from the intended scope of the invention. For example, amino acid modified microcapsules could be attached to specific targeting agents without affecting the intended nature and practice of the invention. All such modifications are intended to be included within the scope of the claims.

REFERENCES

The references listed below are incorporated herein by reference to the extent they supplement, explain, provide a background for or teach methodology, techniques and/or compositions employed herein.

Wright, K. C., Wallace, S., Mosier, B., Mosier, D., *J. Microencapsulation* 5(1), 13–20 (1988).

Wright, K. C., Charnsangavej, C., Wallace, S., Chuang, V. P., Savaraj, N., *Cardiovasc. Internat. Radiol.* 7, 294–298 (1984).

Kawashima, Y., Lin, S. Y., Kasai, A. et al., *Drug Dev. Ind. Pharm. U.S.A.* 10, 467–479 (1984).

Benita, S., Benoit, J. P., Puisieur, F. and Thies, C., *J. Pharm. Sci.* 73, 1721–1724 (1984).

Bechtel, W., *Radiology* 161, 601–604 (1986).

Tice et al., EPO 0302582, Feb. 8, 1989.

Tice, T. R. and Gilley, R. M., *J. Control. Release (Netherlands)* 2, 343–352 (1985).

Smith, A. and Hunneyball, I. M., *Int. J. Pharm. (Netherlands)* 30, 215–220 (1986).

Mosier, U.S. Pat. No. 4,492,720, Jan. 8, 1985.

Jaffe, U.S. Pat. No. 4,272,398, Jun. 9, 1981.

Fong, U.S. Pat. No. 4,933,105, Jun. 12, 1990.

Bechtel, W., Wright, K. C., Wallace, S., Mosier. B., Mosier, D., Mir, S., Kudo, S., *Radiology* 161, 601–604 (1986).

Bruning, J. L. and Kintz, B. L. "Computational Handbook of Statistics'" 2nd Ed., Scott, Foreman and Company, Glenview, Ill. (1977).

Fishman, J. H., *Biochem. Biophys. Res. Commun.* 1983, 110(3), 713–718.

McCague, R.; Leclercq, G.; Jordan, V. C., *J. Med. Chem.* 1988, 31, 1285–1290.

Lowry, O. H.; Rosebrough, N. J.; Farr, A. L.; Randall, R. J., *J. Biol. Chem.* 193, 265–266 (1953).

Zupon, M. A., Fang, S. M. Christensen, J. M. and Peterson, R. V., *J. Pharm. Sci.* 72, 1323–1326 (1983).

Kroschwitz, J. I. in Polymers, Biomaterials and Medical Applications, Wiley and Sons, New York, 5–27 (1989).

Lowry, O. H., Rosenbrough, N. J., Farr, A. L. and Randall, R. J., *J. Biol. Chem.* 193, 265 (1951)

Yang, D. J.. Emran, A. M., Tansey, W., Wallace, S. and Kim, E. E. in New Trends in Radiopharmaceutical Synthesis, Quality Assurance and Regulatory Control, Ed. A. M. Emran, Plenum Press, New York, pp. 67–78 (1991).

Although the present invention has been described in some detail by way of illustration and example for purposes of clarity and understanding, it will be obvious that certain changes and modifications may be practiced within the scope of the claims.

What is claimed is:

1. A method of selective in vivo delivery to uterus tissue comprising administering to a mammal an effective amount of a pharmaceutically acceptable preparation of poly(benzyl L-glutamate) microspheres covalently attached to estrone.

2. The method of claim 1 wherein the estrone is attached with a polylinker.

3. The method of claim 2 wherein the polylinker is a lower alkyl group.

4. The method of claim 1 wherein the microspheres are about 2 to about 6 μm in diameter.

5. The method of claim 1 wherein the microspheres are about 1 μm in diameter.

6. The method of claim 1 wherein the administering is by intravascular injection.

7. The method of claim 1 wherein the microcapsules contain a labeling agent.

8. The method of claim 7 wherein the labeling agent is $^{131}$I-iopanoate.

9. The method of claim 1, further including attaching the microspheres to $^{131}$I-labeled tyramine.

10. Poly(benzyl-L-glutamate) microspheres covalently attached to estrone.

11. The microspheres of claim 10 wherein the estrone is attached through an alkyl linker group.

12. The microspheres of claim 11 wherein the alkyl linker group is ethyl.

13. Poly(benzyl-L-glutamate) microspheres which are covalently linked to tyramine.

14. The microspheres of claim 13 wherein the tyramine is labeled with $^{131}$I.

* * * * *

UNITED STATES PATENT AND TRADEMARK OFFICE
CERTIFICATE OF CORRECTION

PATENT NO. : 5,484,584

DATED : January 16, 1996

INVENTOR(S) : Sidney Wallace, David Yang, Michael Wallace, Chun Li and Li-Ren Kuang It is certified that error appears in the above-identified patent and that said Letters Patent is hereby corrected as shown below:

Title page, item [75], line 5, delete "Sugar Lan" and insert -- Sugar Land--.

Signed and Sealed this

Second Day of April, 1996

Attest:

BRUCE LEHMAN

Attesting Officer         Commissioner of Patents and Trademarks